US012544493B2

(12) United States Patent
Zafiris

(10) Patent No.: US 12,544,493 B2
(45) Date of Patent: Feb. 10, 2026

(54) PERITONEAL DIALYSIS SYSTEM USING INCOMPRESSIBLE FLUID

(71) Applicants: BAXTER INTERNATIONAL INC., Deerfield, IL (US); BAXTER HEALTHCARE SA, Glattpark (CH)

(72) Inventor: John Zafiris, Hawthorn Woods, IL (US)

(73) Assignees: Baxter International Inc., Deerfield, IL (US); Baxter Healthcare SA, Glattpark (CH)

(*) Notice: Subject to any disclaimer, the term of this patent is extended or adjusted under 35 U.S.C. 154(b) by 847 days.

(21) Appl. No.: 17/710,337

(22) Filed: Mar. 31, 2022

(65) Prior Publication Data

US 2022/0313883 A1 Oct. 6, 2022

Related U.S. Application Data

(60) Provisional application No. 63/170,052, filed on Apr. 2, 2021.

(51) Int. Cl.
*A61M 1/14* (2006.01)
*A61M 1/28* (2006.01)

(52) U.S. Cl.
CPC .......... *A61M 1/1524* (2022.05); *A61M 1/155* (2022.05); *A61M 1/1561* (2022.05); *A61M 1/159* (2022.05); *A61M 1/281* (2014.02)

(58) Field of Classification Search
CPC ...... A61M 1/155; A61M 1/159; A61M 1/281; A61M 1/1561; A61M 1/1524; A61M 1/28;

(Continued)

(56) References Cited

U.S. PATENT DOCUMENTS

| | | | | |
|---|---|---|---|---|
| 6,604,908 B1 * | 8/2003 | Bryant | A61M 1/362265 417/27 |
| 7,238,164 B2 * | 7/2007 | Childers | A61M 1/1562 604/4.01 |

(Continued)

FOREIGN PATENT DOCUMENTS

| | | | |
|---|---|---|---|
| CN | 101394879 A * | 3/2009 | A61B 5/0024 |
| DE | 102017114895 A1 * | 1/2019 | A61M 1/14 |

(Continued)

OTHER PUBLICATIONS

International Search Report PCT/US2022/022855 date of mailing Aug. 5, 2022—9 pages.

(Continued)

*Primary Examiner* — Wesley G Harris
(74) *Attorney, Agent, or Firm* — K&L Gates LLP

(57) ABSTRACT

A peritoneal dialysis system includes a cycler having a pumping actuator configured to move an incompressible fluid, a positive pressure actuator, and a control unit; and a disposable set including a chamber including an opening, and at least one plate (e.g., rigid plate) located within the chamber, wherein the control unit is programmed to cause (i) the pumping actuator to move the incompressible fluid to discharge fresh or used dialysis fluid from the chamber through the opening and (ii) the positive pressure actuator to expand the at least one plate to create negative pressure within the chamber to pull fresh or used dialysis fluid into the chamber through the opening.

16 Claims, 9 Drawing Sheets

(58) Field of Classification Search
CPC .... A61M 1/154; A61M 1/14; A61M 5/14224; A61M 5/142; A61M 5/14216; A61M 5/1422; A61M 5/14228; A61M 2005/14268; A61M 5/145; A61M 5/1452; A61M 5/1456; A61M 5/14566; A61M 5/14586; A61M 5/14593; A61M 5/148–155; A61M 2205/12–128
See application file for complete search history.

(56) References Cited

U.S. PATENT DOCUMENTS

| | | | | |
|---|---|---|---|---|
| 2009/0012460 | A1 | 1/2009 | Steck | |
| 2009/0035152 | A1* | 2/2009 | Butterfield | F04B 43/021 417/412 |
| 2012/0232469 | A1* | 9/2012 | Medina | A61M 1/155 604/28 |
| 2019/0099534 | A1 | 4/2019 | McGill et al. | |
| 2022/0054723 | A1* | 2/2022 | Zafiris | A61M 1/1601 |

FOREIGN PATENT DOCUMENTS

| | | | | | |
|---|---|---|---|---|---|
| WO | WO-9420153 | A2 * | 9/1994 | | A61M 1/28 |
| WO | WO-2019007992 | A1 * | 1/2019 | | A61M 1/14 |

OTHER PUBLICATIONS

Written Opinion PCT/US2022/022855 date of mailing Aug. 5, 2022—15 pages.

* cited by examiner

PERITONEAL DIALYSIS SYSTEM USING INCOMPRESSIBLE FLUID

PRIORITY CLAIM

This application claims priority to and the benefit of U.S. Provisional Application No. 63/170,052, filed Apr. 2, 2021, having the same title as above, the entire contents of which are incorporated herein by reference and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal chamber, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending upon the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

It is accordingly desirable to provide a relatively simple, compact APD machine, which operates a simple and cost effective disposable set.

SUMMARY

The present disclosure relates to an automated peritoneal dialysis ("APD") machine or cycler, which in one primary embodiment is part of a mechanically driven system that uses one or more incompressible fluids to move fresh dialysis fluid from a source to a patient and used dialysis fluid from the patient to a drain. The APD system includes a disposable set having a flexible outer pouch, e.g., made of two welded plastic sheets, which form two chambers that are in dialysis fluid communication with each other. A flexible inner pouch is provided inside of the flexible outer pouch and likewise forms two chambers, one in each of the two chambers of the outer pouch, and which are in incompressible fluid communication with each other. That is, the chambers of the inner pouch are filled with an incompressible fluid, such as saline, water, dialysis fluid or a medically safe oil.

One of the pairs of outer and inner chambers forms a positive pressure set of chambers, while the other pair of outer and inner chambers forms a fresh and used dialysis fluid pumping set of chambers. The outer and inner chambers of the positive pressure set have the same shape in one embodiment, e.g., a circular pouch shape wherein the inner chamber is slightly smaller than the outer chamber so as to be able to fit inside of the outer chamber. The outer chamber of the pumping set may likewise have a circular pouch shape and, for example, be sized the same as the outer chamber of the positive pressure set.

The inner chamber of the pumping set is different and in one embodiment includes inflatable volumes that are in incompressible fluid communication with each other. The volumes however leave space for fresh or used dialysis fluid to flow between the volumes and into an interior of the outer chamber of the pumping set to load the pumping set of chambers with fresh or used dialysis fluid in preparation for the next pump-out stroke. First and second rigid plates, e.g., slightly bowed to form a shield shape, are placed above and below the incompressible fluidly connected volumes, so that when the volumes are filled with the incompressible disposable fluid, e.g., saline or other listed above, the plates are spread apart from one another within the outer flexible chamber, causing a negative pressure to form between the plates, pulling fresh or used dialysis fluid into the pumping set of chambers.

The volumes are in one embodiment spheres that are fluidly connected via small tubes extending between the spheres. The spheres may be connected together via the small tubes so as to form a toroid or ring shape having an overall outer diameter that fits inside of the outer chamber of the pumping set of chambers. The toroidal ring leaves the inside of the ring open to receive and dispense fresh or used dialysis fluid.

The outer chamber of the pumping set of chambers is connected fluidly to a plurality of fluid tubes or lines extending to dialysis fluid supply containers, the patient and to a drain, such as a drain container or house drain. The overall disposable set is accordingly relatively simple using primarily flexible plastic components and the rigid plates.

The APD machine or cycler may include an openable and closeable, e.g., hinged, clamshell, wherein each clamshell half defines rigid inwardly projected domes that accept the positive pressure set of chambers and the dialysis fluid pumping set of chambers, respectively, allowing the outer flexible chambers of positive pressure and pumping sets to expand and be pushed closed within the respective domes. The clamshell halves may be made of metal, plastic or a combination of same. One of the clamshell halves is provided with a positive pressure linear actuator and a pumping linear actuator. Alternatively, one of the clamshell halves is provided with the positive pressure linear actuator, while the other clamshell half is provided with the pumping linear actuator.

The linear actuators may each include, for example, a stepper motor whose output shaft is connected to a lead or ball screw that turns to translate a member back and forth. The member is connected to a piston shaft that drives a piston head back and forth within a cylinder. The motor may be fitted with an encoder that accurately records the amount of rotational travel of the output shaft from which an accurate amount of travel of the piston head may be determined. Knowing the amount of travel of the piston head and the internal diameter of the cylinder enables an accurate volume displacement to be determined.

The cylinders in an embodiment are filled with an incompressible driving fluid, such as oil, between the piston head and a durable and reusable flexible diaphragm, which is sealed permanently to the clamshell so as to cover one of the domes formed in the clamshell. The linear actuators are energized together so that (i) as one linear actuator extends its piston head, forcing incompressible driving fluid (e.g., oil) into the respective clamshell dome and driving the disposable incompressible fluid (e.g., saline) from the respective set of chambers to the other set of chambers, (ii) the other linear actuator retracts its piston head, allowing the incompressible driving fluid (e.g., oil) into its cylinder and thereby allowing the disposable incompressible fluid (e.g., saline) to enter its associated set of chambers.

To pull fresh or used dialysis fluid into the outer chamber of the pumping set of disposable chambers, the positive pressure linear actuator extends its piston head while the pumping linear actuator retracts its piston head. To push fresh or used dialysis fluid from the outer chamber of the pumping set of disposable chambers, the positive pressure linear actuator retracts its piston head while the pumping linear actuator extends its piston head. Valves, such as electrically actuated pinch valves are sequenced to selectively open or occlude the lines or tubes extending from outer chamber of the pumping set of disposable chambers to determine (i) which source, e.g., fresh dialysis fluid from a supply container or used dialysis fluid from the patient, is used for filling the outer chamber of the pumping set of disposable chambers and (ii) which destination, e.g., fresh dialysis fluid to the patient or used fluid to a drain, is used for emptying the outer chamber of the pumping set of disposable chambers.

It is contemplated to use batch or inline heating with the APD systems of the present disclosure. If inline heating is used, the inline heater may operate with the patient line and heat dialysis fluid as it is delivered to the patient. If batch heating is used, an initial dialysis fluid supply container may be placed on a batch heater. After the fresh dialysis fluid is pumped from the initial dialysis fluid supply container, fresh dialysis fluid may be pumped from a second or third supply container to the first supply container, e.g., during a patient dwell, for heating in preparation for a next patient fill. In the case of batch heating then, an additional destination for fresh dialysis fluid may be the initial supply container for heating.

A control unit for the APD cycler is provided for powering and controlling the linear actuators, pinch valves and heater. One or more sensors may be provided, such as one or more pressure sensors operable with the pumping linear actuator for reasons discussed next and one or more temperature sensors operable with the inline or batch heater. The control unit receives signals from the sensors to control the linear actuators and the heater. The control unit also operates bidirectionally with a user interface to output treatment data to the user interface and to receive commands from same.

As described above, the APD systems of the present disclosure may operate with three incompressible fluids including fresh or used dialysis fluid, an incompressible driving fluid, such as oil, and a disposable incompressible fluid, such as saline. In theory, when only the three incompressible fluids interact, the amount of incompressible driving fluid discharged from the cylinder of the pumping linear actuator equals the amount of fresh or used dialysis fluid discharged from the outer chamber of the pumping set of chambers to a desired destination. Summing such volumes over the course of a pumping sequence via the control unit provides a total fresh or used dialysis fluid pumped.

It is possible however that air may be present in the system, e.g., between the inner and outer disposable chambers or in the dialysis fluid. If so, and if some air is discharged from the outer chamber, then the volume calculation may be inaccurate, albeit slightly. It is accordingly contemplated for the control unit to run a quick test sequence before and after the discharge stroke of the pumping linear actuator to determine if any air has been delivered. The test in both before and after instances involves closing all pinch valves such that the APD system is fluidically closed. Next, the linear actuators are energized to move a small amount of the incompressible driving fluid, e.g., 15 milliliters ("ml"), during and after which a pressure measurement is taken, e.g., via a pressure sensor associated with the cylinder of the pumping linear actuator. If the pressure measurements taken during the movement immediately spike then it may be assumed that no or negligible air exists. Otherwise, the ideal gas law is used to determine the amount of air present in fluidically closed system. If the amount of air determined in the test after the discharge stroke is determined to be less than the amount of air determined in the test before the discharge stroke, then it is assumed that the difference is the amount has been delivered in the discharge stroke, wherein the control unit subtracts the delivered air volume from the dialysis fluid discharge volume.

In an embodiment, the same pressure sensor associated with the cylinder of the pumping linear actuator is used during treatment to ensure that positive pumping pressures are maintained within safe limits. The control unit receives positive pressure signals from the pressure sensor and uses same as feedback to control the speed of movement of the piston head of the pumping linear actuator to ensure safe positive pressure dialysis fluid pumping to the patient (wherein the speed of the piston head of the positive pressure linear actuator is set by the control unit to follow that of the piston head of the pumping linear actuator). The control unit in an embodiment receives negative pressure signals from a separate pressure sensor associated with the positive pressure actuator, which creates negative fluid pressure in the outer fluid chamber, and wherein the control unit uses same as feedback to control the speed of movement of the piston head of the positive pressure linear actuator to ensure safe negative pressure dialysis fluid pumping from the patient (wherein the speed of the piston head of the pumping linear actuator is set by the control unit to follow that of the piston head of the positive pressure linear actuator).

A second primary embodiment of the present disclosure operates in much the same way as the first primary embodiment, including the provision of a linear actuator using an incompressible driving fluid for pumping fresh and used dialysis fluid into and out of a chamber of a disposable set.

The chamber again includes one or more rigid expander plates for opening the chamber to receive fresh or used dialysis fluid. The before and after discharge stroke tests for air and resulting air delivered compensation are also provided. The same pinch valves, inline or batch heating, pressure and temperature sensing controlled by and/or outputting to a control unit may likewise be employed.

The primary differences are (i) the disposable incompressible fluid is not needed or used and thus the disposable set does not require inner and outer chambers and (ii) the positive pressure linear actuator of the first primary embodiment is replaced with an expander motor that drives a mechanical linkage to expand the one or more rigid expander plates for opening the chamber to receive fresh or used dialysis fluid. The one or more rigid expander plates is connected mechanically to a disposable linkage. When the disposable set is mounted into the APD cycler, the disposable linkage is placed in mechanical communication with the motor-driven mechanical linkage of the cycler. The disposable linkage may include lever arms in rotatable communication with the one or more rigid expander plates, and in one embodiment the motor-driven mechanical linkage of the cycler is actuated so as to pull the lever arms apart, which in turn expands or pulls apart the one or more rigid expander plates within the chamber, creating negative pressure within the chamber for drawing in fresh or used dialysis fluid.

As with the first primary embodiment, the same pressure sensor associated with the cylinder of the pumping linear actuator is provided with the second primary embodiment and is used during treatment to ensure that positive pumping pressures are maintained within safe limits. Here again, the control unit receives positive pressure signals from the pressure sensor and uses same as feedback to control the speed of movement of the piston head of the pumping linear actuator to ensure safe positive pressure dialysis fluid pumping to the patient (wherein the speed of the expander motor driving the mechanical linkage is set by the control unit to follow that of the piston head of the pumping linear actuator). The control unit may be configured to derive negative pressure based on a measured force exerted on the lever arms, wherein the negative pressure is calculated based on the measured force and the dimensions of the lever arms and the area of the associated expander plates. The exerted force may be measured using one or more load cells, or by measuring the power applied to the motor (with more limited precision and using a permanent magnet motor), which has a calibratable transfer function that can correlate motor torque versus power. In either case, the control unit uses the derived negative pressure as feedback to control the speed of movement of the expander motor driving the mechanical linkage to ensure safe negative pressure dialysis fluid pumping from the patient (wherein the speed of the piston head of the pumping linear actuator is set by the control unit to follow that of the expander motor driving the mechanical linkage).

In light of the disclosure set forth herein, and without limiting the disclosure in any way, in a first aspect of the present disclosure, which may be combined with any other aspect, or portion thereof, a peritoneal dialysis system comprises a cycler including a pumping actuator configured to move an incompressible fluid, a positive pressure actuator, and a control unit; and a disposable set including a chamber including an opening, and at least one plate located within the chamber, wherein the control unit is programmed to cause (i) the pumping actuator to move the incompressible fluid to discharge fresh or used dialysis fluid from the chamber through the opening and (ii) the positive pressure actuator to expand the at least one plate to create negative pressure within the chamber to pull fresh or used dialysis fluid into the chamber through the opening.

In a second aspect of the present disclosure, which may be combined with any other aspect, or portion thereof, the pumping actuator includes a linear actuator including a piston head that moves back and forth within a cylinder, the cylinder holding the incompressible fluid between the piston head and a diaphragm.

In a third aspect of the present disclosure, which may be combined with any other aspect, or portion thereof, the diaphragm is sealed to a dome formed in the cycler, the dome in incompressible fluid communication with the cylinder.

In a fourth aspect of the present disclosure, which may be combined with any other aspect, or portion thereof, the linear actuator includes a motor that translates a member along a rotational to translational conversion device, and wherein the member is in mechanical communication with a piston shaft that moves the piston head.

In a fifth aspect of the present disclosure, which may be combined with any other aspect, or portion thereof, the control unit is configured to determine a volume of incompressible fluid moved by the pumping actuator and take the volume of incompressible fluid moved as a volume of fresh or used dialysis fluid discharged from the chamber.

In a sixth aspect of the present disclosure, which may be combined with any other aspect, or portion thereof, the control unit is configured to determine the volume of incompressible fluid moved by the pumping actuator by multiplying a sensed movement of the pumping actuator by a cross-sectional area of the pumping actuator.

In a seventh aspect of the present disclosure, which may be combined with any other aspect, or portion thereof, the control unit is configured to reduce the volume of fresh or used dialysis fluid discharged from the chamber by a volume of air discharged from the chamber along with the fresh or used dialysis fluid, and wherein the control unit is further configured to determine the volume of air by taking pressure readings before and after discharging the volume of fresh or used dialysis fluid and using the pressure readings in before and after calculations involving the ideal gas law.

In an eighth aspect of the present disclosure, which may be combined with any other aspect, or portion thereof, the positive pressure pumping actuator includes a linear actuator including a piston head that moves back and forth within a cylinder, the cylinder holding its own incompressible fluid between the piston head and a diaphragm.

In a ninth aspect of the present disclosure, which may be combined with any other aspect, or portion thereof, the diaphragm is sealed to a dome formed in the cycler, the dome in incompressible fluid communication with the cylinder.

In a tenth aspect of the present disclosure, which may be combined with any other aspect, or portion thereof, the linear actuator includes a motor that translates a member along a rotational to translational conversion device, and wherein the member is in mechanical communication with a piston shaft that moves the piston head.

In an eleventh aspect of the present disclosure, which may be combined with any other aspect, or portion thereof, the chamber is an outer chamber, and which includes an inner chamber located within the outer chamber, and wherein the positive pressure pumping actuator is configured to force a second incompressible fluid into the inner chamber to in turn expand the at least one plate to create negative pressure within the chamber to pull fresh or used dialysis fluid into the chamber through the opening.

In a twelfth aspect of the present disclosure, which may be combined with any other aspect, or portion thereof, the inner chamber and the outer chamber form a pumping set of chambers, and wherein the disposable cassette includes a second inner chamber located within a second outer chamber, the second inner and outer chambers forming a positive pressure set of chambers, the second inner chamber holding the second incompressible fluid, and wherein the positive pressure pumping actuator is configured to compress the positive pressure set of chambers to force the second incompressible into the inner chamber of the pumping set of chambers.

In a thirteenth aspect of the present disclosure, which may be combined with any other aspect, or portion thereof, the inner chamber includes a plurality of inflatable volumes in incompressible fluid communication, the inflatable volumes collectively sized to allow fresh or used dialysis fluid to flow into the outer chamber around the outsides of the inflatable volumes.

In a fourteenth aspect of the present disclosure, which may be combined with any other aspect, or portion thereof, the inflatable volumes include inflatable spheres.

In a fifteenth aspect of the present disclosure, which may be combined with any other aspect, or portion thereof, the inflatable volumes collectively form a toroidal ring inside of the outer chamber.

In a sixteenth aspect of the present disclosure, which may be combined with any other aspect, or portion thereof, the positive pressure pumping actuator includes a motor-driven mechanical linkage, the disposable set including a disposable linkage that is placed in mechanical communication with the motor-driven mechanical linkage of the cycler, the disposable linkage configured to expand the at least one plate to create negative pressure within the chamber when the disposable linkage is actuated by the mechanical linkage.

In a seventeenth aspect of the present disclosure, which may be combined with any other aspect, or portion thereof, the disposable linkage includes a plurality of lever arms in rotatable communication with the at least one plate.

In an eighteenth aspect of the present disclosure, which may be combined with any other aspect, or portion thereof, the motor-driven mechanical linkage is configured to pull the lever arms apart, which in turn expands the at least one plate to create negative pressure within the chamber to pull fresh or used dialysis fluid into the chamber through the opening.

In a nineteenth aspect of the present disclosure, which may be combined with any other aspect, or portion thereof, the chamber includes a plurality of openings in fresh or used dialysis fluid communication with different sources and destinations.

In a twentieth aspect of the present disclosure, which may be combined with any other aspect, or portion thereof, a peritoneal dialysis system comprises a cycler including a pumping actuator configured to move a first volume of a first incompressible fluid, a positive pressure actuator configured to move a second volume of the first incompressible fluid, and a control unit; and a disposable set including an outer chamber including an opening, at least one plate located within the outer chamber, an inner chamber located within the outer chamber so as to contact the at least one plate, a positive pressure chamber in incompressible fluid communication with the inner chamber, the inner chamber and the positive pressure chamber hold a second incompressible fluid, wherein the control unit is programmed to cause (i) the positive pressure actuator to move the second volume of the first incompressible fluid to close positive pressure chamber, thereby forcing the second incompressible fluid into the inner chamber to expand the at least one plate to create negative pressure within the outer chamber to pull fresh or used dialysis fluid into the outer chamber through the opening, and (ii) the pumping actuator to move the first volume of the first incompressible fluid to close the outer chamber, thereby forcing fresh or used dialysis fluid out of the outer chamber through the opening.

In a twenty-first aspect of the present disclosure, which may be combined with any other aspect, or portion thereof, a peritoneal dialysis system comprises a cycler including a pumping actuator configured to move an incompressible fluid, a motor-driven linkage, and a control unit; and a disposable set including a chamber including an opening, at least one plate located within the chamber, a disposable linkage in mechanical communication with the at least one plate, wherein the control unit is programmed to cause (i) motor-driven linkage to move the disposable linkage, thereby expanding the at least one plate to create negative pressure within the chamber to pull fresh or used dialysis fluid into the chamber through the opening, and (ii) the pumping actuator to move the incompressible fluid to close the chamber, thereby forcing fresh or used dialysis fluid out of the outer chamber through the opening.

In a twenty-second aspect of the present disclosure, which may be combined with any other aspect, or portion thereof, any of the features, functionality and alternatives described in connection with any one or more of FIGS. 1 to 12 may be combined with any of the features, functionality and alternatives described in connection with any other of FIGS. 1 to 12.

It is accordingly an advantage of the present disclosure to provide a relatively volumetrically accurate automated peritoneal dialysis ("APD") cycler.

It is another advantage of the present disclosure to provide an APD cycler that achieves relatively precise pressure control.

It is a further advantage of the present disclosure to provide a relatively quiet APD cycler.

It is still another advantage of the present disclosure to provide an APD cycler that is safe regarding the infusion of the patient with air.

It is still a further advantage of the present disclosure to provide an APD system that is able to build motive fluid or pumping pressure in a relatively simple manner.

It is yet another advantage of the present disclosure to provide an APD system that employs a relatively low cost disposable set.

Still further, it is an advantage of the present disclosure to provide an APD system that is capable of pumping a high flowrate using a relatively small disposable.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

First Primary Embodiment

Figure 1:
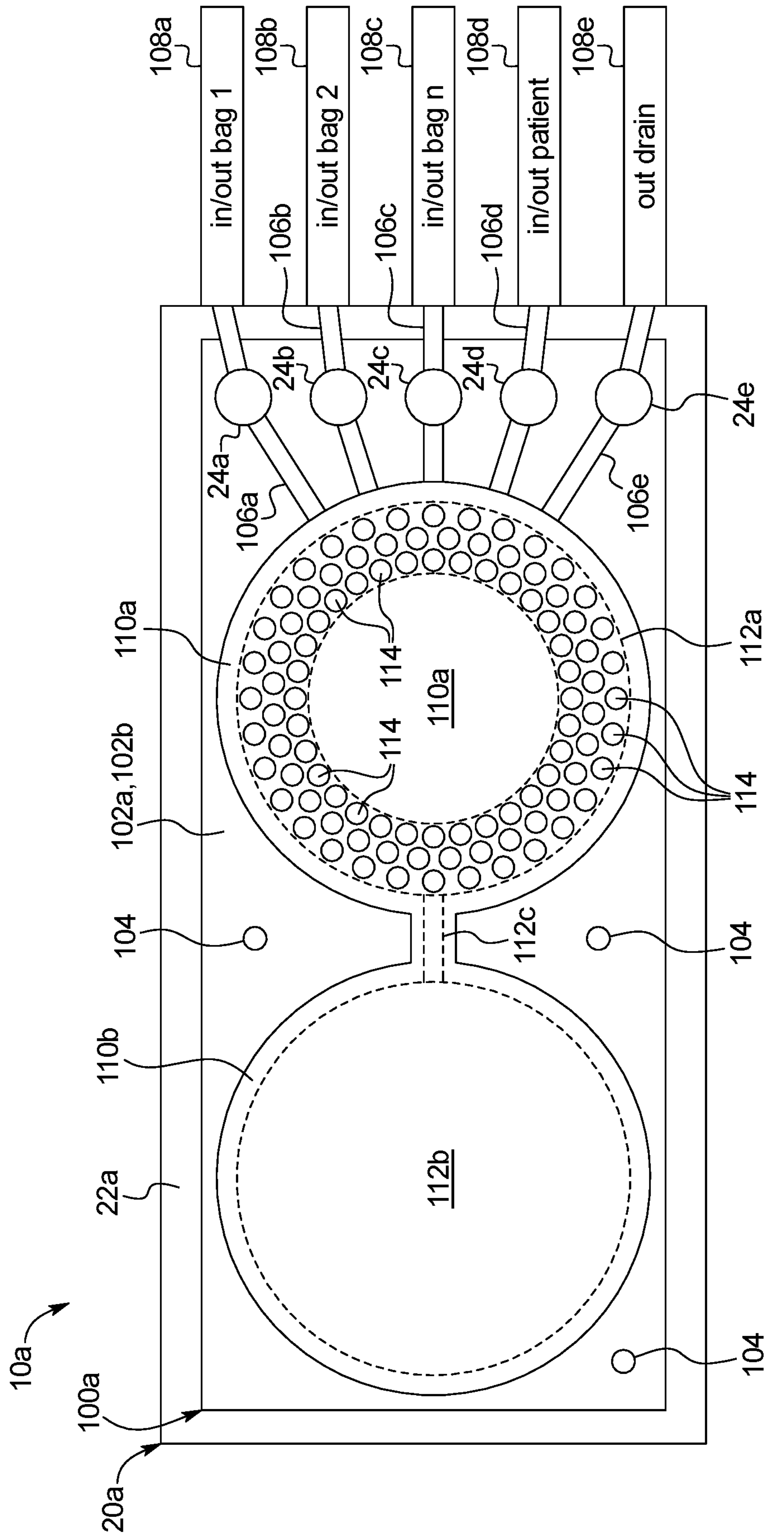
FIG. 1 is a top plan view of a first primary embodiment for an automated peritoneal dialysis ("APD") cycler and disposable set of the present disclosure.

Referring now to the drawings and in particular to FIGS. 1 to 5, a first automated peritoneal dialysis ("APD") system 10*a* of the present disclosure includes an APD machine or cycler 20*a* that operates with a disposable set 100*a*. APD machine or cycler 20*a* includes a housing 22*a* onto or into which disposable set 100*a* is placed for treatment. Housing 22*a* in the illustrated embodiment is a rigid structure, which may be made of a polymer or plastic, such as, polyvinyl chloride ("PVC"), polyethylene ("PE"), polyurethane ("PU") and/or polycarbonate ("PC"), and/or of metal, such as stainless steel, steel or aluminum. Disposable set 100*a* may include flexible, rigid and/or semirigid structures that may be made of a polymer or plastic, such as any one or more of the polymers or plastics listed above.

In the illustrated embodiment, disposable set 100*a* is at least substantially horizontally disposed on or within housing 22*a* of cycler 20*a*. Disposable set 100*a* includes outer flexible sheets 102*a* and 102*b*. Flexible sheets 102*a* and 102*b* are sealed together, e.g., ultrasonically sealed, heat sealed or solvent bonded, to form chambers for pumping fresh and used dialysis fluid (discussed below), registration holes or apertures 104 for aligning disposable set 100*a* onto housing 22*a*, and dialysis fluid pathways 106*a* to 106*e* for pumping from and to different dialysis fluid sources and destinations, respectively. In an alternative embodiment, dialysis fluid pathways 106*a* to 106*e* may instead be ports that connect to the ends of lines or tubes 108*a* to 108*e*. Tubes 108*a* to 108*e* are, respectively, dialysis fluid supply container tubes 108*a* to 108*c* leading to dialysis fluid supply containers (not illustrated), a patient tube 108*d* leading to a patient connector (not illustrated), and a drain tube 108*e* leading to a drain, such as a drain container or a house drain, e.g., toilet, bathtub, etc.

Dialysis fluid pathways 106*a* to 106*e* in the illustrated embodiment form valve seats that operate with cycler valves 24*a* to 24*e*, respectively, which may be electrically actuated solenoid punch valves. Pinch valves 24*a* to 24*e* in one embodiment are spring closed and electrically actuated open for fail safe operation upon power loss. It should be appreciated that while dialysis fluid pathways 106*a* to 106*e* are illustrated as individually communicating fluidly with outer chamber 110*a*, dialysis fluid pathways 106*a* to 106*e* alternatively communicate with a manifold line, which in turn communicates with outer chamber 110*a* via a single inlet/outlet.

Figure 2:
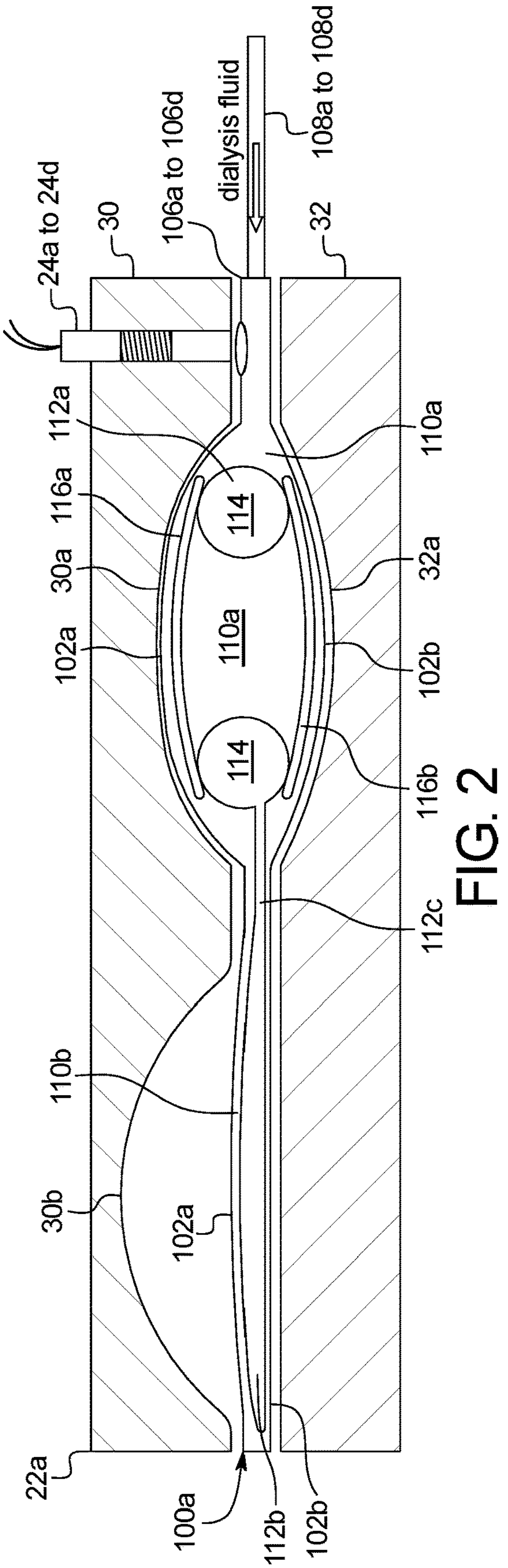
FIGS. 2 and 3 are elevation sectioned views of a relevant portion of the cycler and disposable set of the first primary embodiment of present disclosure, wherein the disposable set is in different states of operation.
Figure 3:
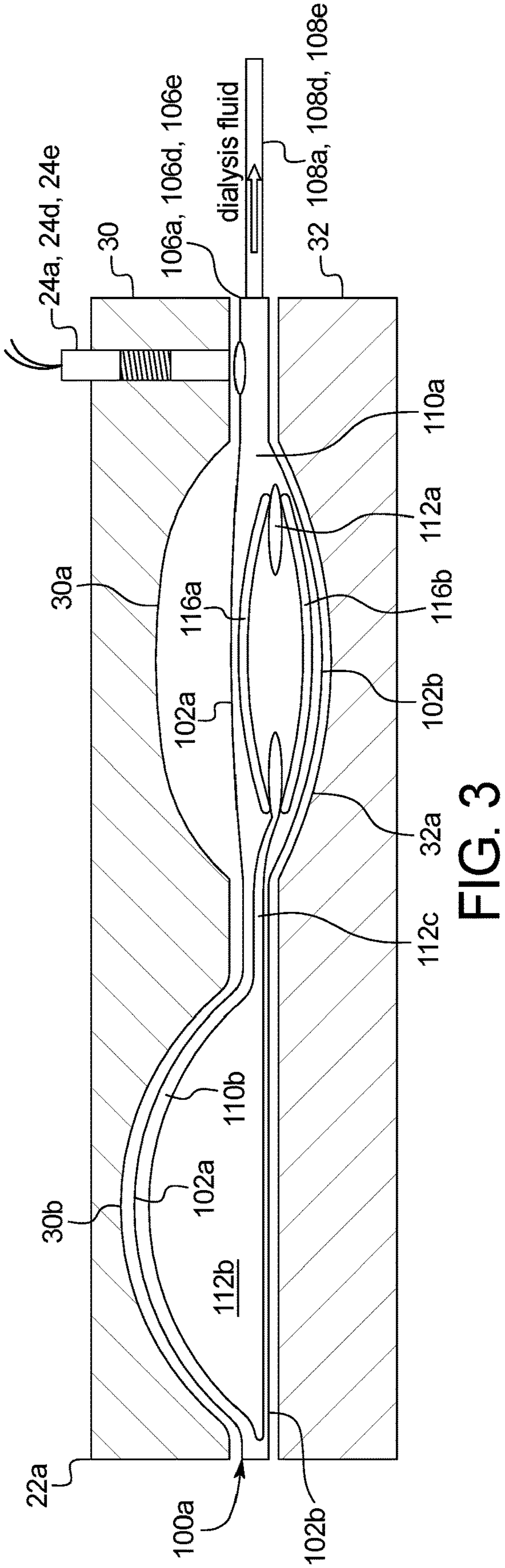

FIGS. 1 to 3 illustrate disposable set 100*a* and its mounting for operation within housing 22*a* in detail. FIGS. 2 and 3 illustrate that housing 22*a* in an embodiment includes clamshell halves 30 and 32 that closed together about disposable set 100*a*. Clamshell halves 30 and 32 may hinge together and apart or translate together and apart. In the illustrated embodiment, upper clamshell half 30 includes or defines inwardly extending domes 30*a* and 30*b*, while lower clamshell half 32 includes or defines an inwardly extending dome 32*a*. Domes 30*a*, 32*a* and dome 30*b* are aligned with corresponding chambers of disposable set 100*a*.

In particular, flexible sheets 102*a* and 102*b* are sealed to form a first outer chamber 110*a* that fits into domes 30*a* and 32*a* and a second outer chamber 110*b* that fits inside dome 30*b*. As described below, first outer chamber 110*a* receives fresh and used dialysis fluid, while second outer chamber 110*b* does not receive fluid and instead covers a second inner chamber. Second outer chamber 110*b* may accordingly be eliminated if desired but does provide protection against a leak forming in the second inner chamber.

FIGS. 2 and 3 illustrate that disposable set 100*a* also includes a first inner chamber 112*a*, which is located within first outer chamber 110*a*, and a second inner chamber 112*b*, which is located within second outer chamber 110*b*. First and second inner chambers 112*a* and 112*b* are formed via sealed (ultrasonic, heat or solvent) flexible plastic sheets so as communicate fluidly with each other via passageway 112*c* illustrated in FIGS. 1 to 3. In an embodiment, flexible sheets 102*a* and 102*b* forming outer chambers 110*a* and 110*b* are sealed (ultrasonic, heat or solvent) to the sheets forming inner chambers 112*a* and 112*b* at a location between outer chambers 110*a* and 110*b* to prevent fresh or used dialysis from flowing from outer chamber 110*a* to outer chamber 110*b*.

Inner chambers 112*a* and 112*b* hold a disposable incompressible fluid, such as saline, water, dialysis fluid or a medically safe oil. The disposable incompressible fluid is able to flow back and forth between inner chambers 112*a* and 112*b*. Inner chamber 112*b* is circular in one embodiment and may be sized so as to be slightly smaller than outer chamber 110*b*. Inner and outer chambers 112*b* and 110*b* flex open and closed together as illustrated in FIGS. 2 and 3.

Inner chamber 112*a* on the other hand is formed of fluidly connected volumes 114, which when expanded may form spheres as illustrated in FIGS. 1 and 2. Volumes or spheres 114 are connected together fluidly so that the disposable incompressible fluid, e.g., saline, may flow into and out of each of the volumes of inner chamber 112*a*. Volumes or spheres 114 are shaped to allow fresh or used dialysis fluid to flow between and past the volumes. As illustrated in FIG. 1, volumes or spheres 114 form a toroidal ring that allows fresh or used dialysis fluid to flow into the middle of the ring, forming a primary fluid holding portion of outer chamber 110*a*.

FIGS. 2 and 3 illustrate that rigid plates 116*a* and 116*b*, e.g., flat circular or bowed circular (shield) shaped plates, are located between volumes or spheres 114 and flexible sheets 102*a* and 102*b* that form outer chamber 110*a*. Rigid plates 116*a* and 116*b* may be (i) sealed (ultrasonic, heat or solvent bonded) to the outsides of volumes or spheres 114, (ii) sealed to the insides of flexible sheets 102*a* and 102*b*, respectively, or (iii) not be sealed and instead be held in place via friction between outer chamber 110*a* and inner chamber 112*a*. In any case, rigid plates 116*a* and 116*b* help flexible sheets 102*a* and 102*b* to expand uniformly to conform with cycler domes 30*a* and 32*a*, respectively, when the disposable incompressible fluid, e.g., saline, is driven into inner chamber 112*a* to inflate volumes or spheres 114.

FIG. 2 illustrates that when the disposable incompressible fluid, e.g., saline, is driven into inner chamber 112*a* to inflate volumes or spheres 114, rigid plates 116*a* and 116*b* are pushed apart or expanded to in turn expand flexible sheets 102*a* and 102*b*. Such action creates a negative pressure within outer chamber 110*a*, drawing (i) fresh dialysis fluid into outer chamber 110*a* (as indicated by the arrow) via supply pathways 106*a* to 106*c* or (ii) used dialysis fluid into outer chamber 110*a* (as indicated by the arrow) via patient pathway 106*d*. Corresponding pinch valve 24*a* to 24*d* is open accordingly.

FIG. 3 illustrates that when the disposable incompressible fluid, e.g., saline is driven from inner chamber 112*a* into inner chamber 112*b* to deflate volumes or spheres 114, rigid plates 116*a* and 116*b* are pushed together or contracted to in turn pushed together or contract flexible sheets 102*a* and 102*b*. Such action creates a positive pressure within outer chamber 110*a*, pushing (i) fresh dialysis fluid from outer chamber 110*a* (as indicated by the arrow) via supply pathway 106*a* (for batch heating) or patient pathway 106*d* or (ii) used dialysis fluid from outer chamber 110*a* (as indicated by the arrow) via drain pathway 106*e*. Corresponding pinch valve 24*a*, 24*d* or 24*e* is open accordingly. As described herein, where batch heating is provided, one of the supply containers, such as the supply container connected to supply container tube 108*a*, may be a dedicated batch heating container. In such a case, the dedicated batch heating container becomes a fresh dialysis fluid destination.

Figure 4:
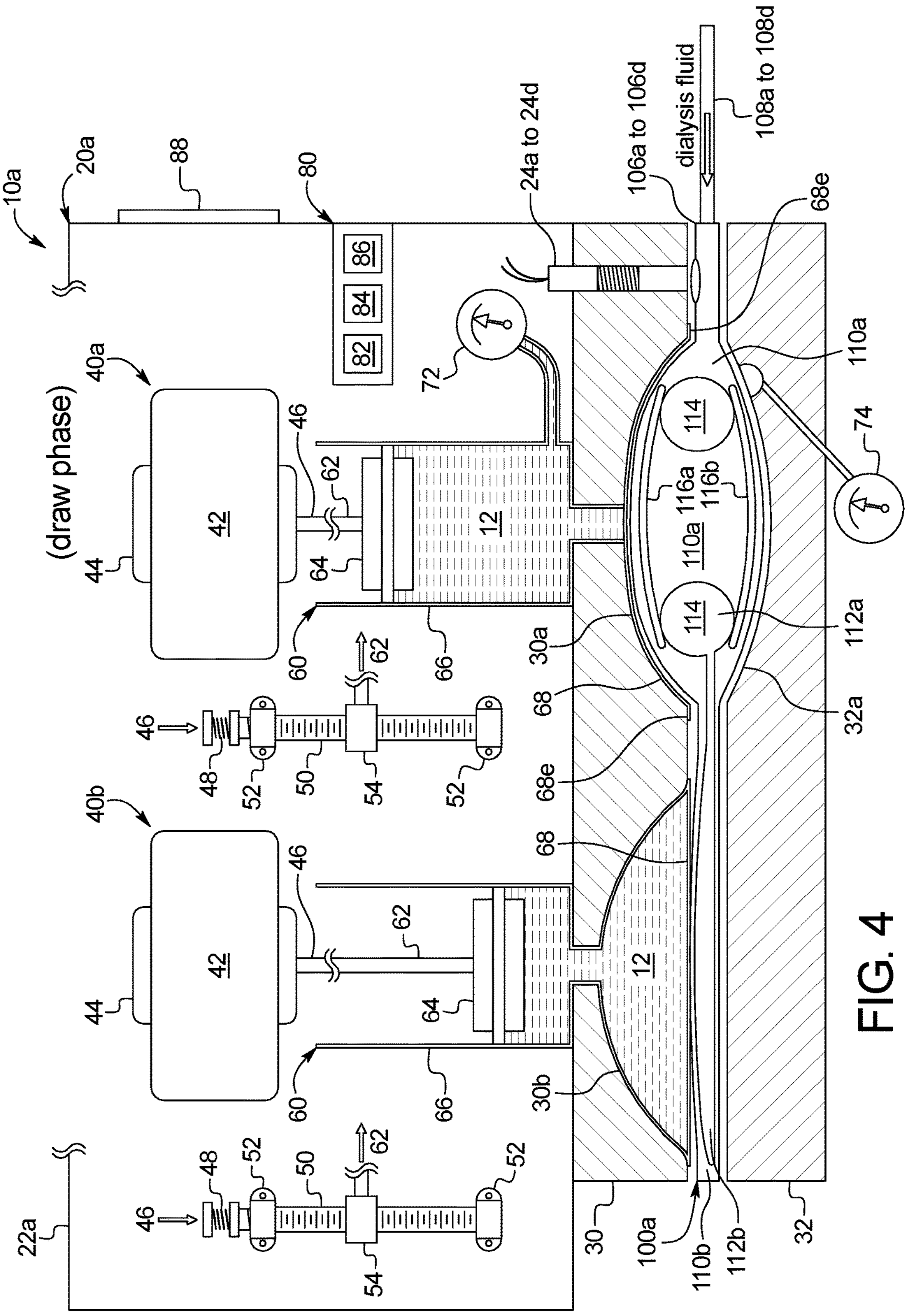
FIG. 4 is an elevation sectioned view of the cycler and disposable set of the first primary embodiment of present disclosure operating in a draw phase.
Figure 5:
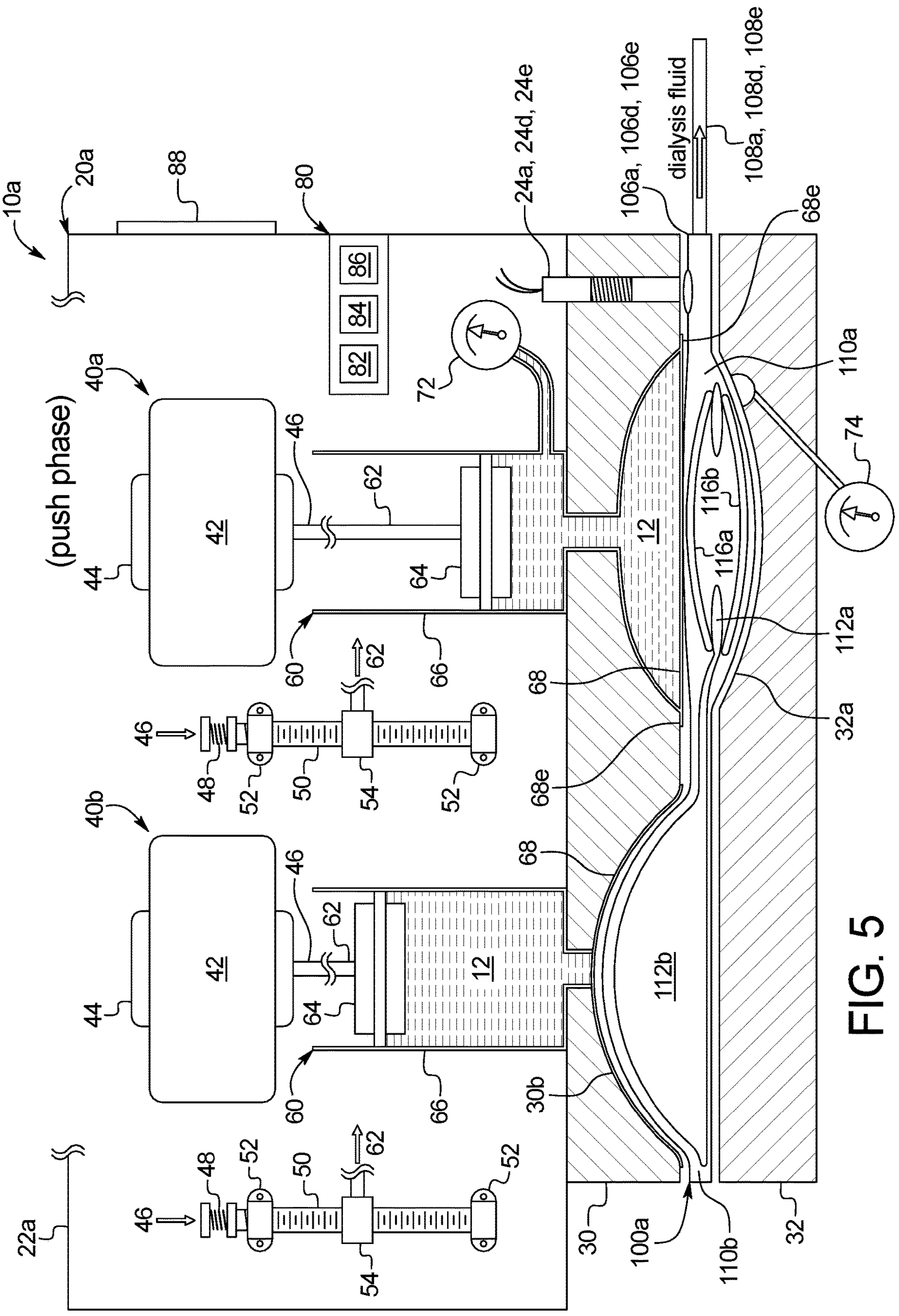
FIG. 5 is an elevation sectioned view of the cycler and disposable set of the first primary embodiment of present disclosure operating in a push or discharge phase.

FIGS. 4 and 5 illustrate one example set of equipment for achieving the pumping sequences of FIGS. 2 and 3, wherein the disposable incompressible fluid, e.g., saline is pushed back and forth within inner chambers 112*a* and 112*b*. Inner chamber 112*a* and outer chamber 110*a* may be said to form a pumping set of chambers, while inner chamber 112*b* and outer chamber 110*b* may be said to form a positive pressure set of chambers. FIGS. 4 and 5 illustrate that cycler 10*a* in the illustrated embodiment includes a pumping actuator 40*a* operating with the pumping set of chambers of inner and outer chambers and a positive pressure actuator 40*b* operating with the pumping set of chambers of inner and outer chambers. Pumping actuator 40*a* and positive pressure actuator 40*b* are largely the same in the illustrated embodiment, wherein each includes a linear actuator.

The linear actuators of positive pressure actuators 40*a* and 40*b* each include a motor 42, such as a stepper, servo, brushed or brushless AC or DC motor operable with an encoder 44, which outputs a signal indicative of how much a shaft 46 of motor 42 has actually turned. In an embodiment, shaft 46 is connected to a coupler 48, which may be a flexible coupler configured to provide translational accuracy. Coupler 48 is connected at its other end to a ball or lead screw 50, which is fixed at both ends to housing 22*a* of cycler 20*a* via bearings 52. Motor 42 turns shaft 46, coupler 48 and ball or lead screw 50 a commanded number of revolutions and/or partial revolution. A member 54 threadingly connected to ball or lead screw 50 is in turn translated a precise distance. Encoder outputs the actual turns of motor 42, which is converted to an actual distance traveled by member 54 knowing the pitch of ball or lead screw 50.

Member 54 is connected to a shaft 62 of a piston/cylinder 60 of the linear actuator. Shaft 62 terminates at or is connected to a piston head 64, which is sealed inside of a cylinder 66 having a known and constant internal diameter. Cylinder 66 is filled with an incompressible driving fluid 12, such as oil (e.g., silicone oil, or any of the fluids listed for the disposable incompressible fluid), located between the opposing side of piston head 64 from piston shaft 62 and a durable, reusable flexible diaphragm 68, which may for example be made of silicone or polyurethane rubber. Durable, reusable flexible diaphragm 68 is sealed at its edge 68*e*, e.g., circular edge, to upper clamshell half 30 so as to cover inwardly extending domes 30*a* and 30*b*, e.g., via adhesive and/or mechanical sealing. Durable, reusable flexible diaphragm 68 prevents incompressible driving fluid 12 from escaping cycler 20*a*.

A pressure sensor 72 in the illustrated embodiment is positioned so as to measure the pressure of incompressible driving fluid 12 within cylinder 66 of pumping actuator 40*a*. A similar pressure sensor (not illustrated) may also be provided with cylinder 66 of positive pressure actuator 40*b* to monitor negative pumping pressure and to pressure check the integrity of reusable flexible diaphragm 68, e.g., at the beginning of treatment or in between treatments prior to loading disposable set 100*a*. The same integrity test may be performed to test the integrity of flexible diaphragm 68 of pumping actuator 40*a*. Pressure sensor 72 provides positive pressure feedback for controlling the speed and resulting pressure of fresh dialysis fluid delivered to the patient (e.g., three psig or less). The output from pressure sensor 72 is also used in an ideal gas law calculation discussed herein. The similar pressure sensor (not illustrated) provided with cylinder 66 of positive pressure actuator 40*b* is used to provide negative pressure feedback for used dialysis fluid pulled from the patient so as to maintain the negative pressure within a negative patient pressure limit (e.g., −1.5 psig or less).

A temperature sensor 74 in the illustrated embodiment is positioned so as to measure the temperature of any air that may be present in the dialysis fluid within outer chamber 110*a*. Temperature sensor 74, or one or more additional temperature sensor located with a heating mechanism associated with system 10*a* (and system 10*b*), may also be provided for feedback in the control of a dialysis fluid heater to heat fresh dialysis fluid to body temperature or 37° C. for delivery to a patient. It is contemplated to use the feedback from one or more temperature sensor 74 with batch or inline heating of APD system 10*a* (and system 10*b*). If inline heating is used, an inline heater (not illustrated) may operate with patient line 108*d* and heat dialysis fluid as it is delivered to the patient. If batch heating is used, e.g., resistive plate heating, an initial dialysis fluid supply container (e.g., connected to line 108*a*) may be placed on a batch heater (not illustrated). After fresh, heated dialysis fluid is pumped from the initial dialysis fluid supply container, fresh dialysis fluid may be pumped from a second or third supply container (e.g., connected to lines 108*b* and 108*c*) to the first supply container, e.g., during a patient dwell, for heating in preparation for a next patient fill. In the case of batch heating then, an additional destination for fresh dialysis fluid may be the initial supply container for heating, which can be controlled via pressure sensor 72 for operation at a higher system pressure because the patient is not involved.

In the illustrated embodiment of FIGS. 4 and 5, APD machine or cycler 20*a* of system 10*a* includes a control unit 80 (also included with APD machine or cycler 20*b* of system 10*b*). Control unit 80 may include one or more processor 82, one or more memory 84, and a video controller 86 interfacing with a user interface 88, which may include a display screen operating with a touchscreen and/or one or more electromechanical button, such as a membrane switch. User interface 88 may also include one or more speaker for outputting alarms, alerts and/or voice guidance commands. User interface 88 is alternatively or additionally provided as a wireless user interface, such as a tablet or smartphone. Control unit 80 may further include a transceiver and a wired or wireless connection to a network, e.g., the internet, for sending treatment data to and receiving prescription instructions from a doctor's or clinician's server interfacing with a doctor's or clinician's computer.

Control unit 80 is programmed to control motors 42 of actuators 40*a* and 40*b* and to receive signal outputs from motor encoder 44. The signal outputs enable control unit 80 to know how much incompressible driving fluid is moved within cylinders 66. Control unit 80 receives pressure signals from pressure sensor 72 to control dialysis fluid pumping pressure and to know the air pressure within outer chamber 110*a* for the ideal gas law volume calculations discussed herein. Control unit 80 is also programmed to control pinch valves 24*a* to 24*e* (FIG. 1) to pump from a desired source to a desired destination. Control unit 80 also operates the inline or batch heater (not illustrated) as needed to heat fresh dialysis fluid to body temperature via feedback from one or more temperature sensor 94 inputted into a heater algorithm, such as a proportional, integral and derivative ("PID") algorithm.

Pressure control for each operation step of system 10*a* (and system 10*b*) discussed herein may be initially attempted by delivering a designated (e.g., via a look-up table stored in one or more memory 84) electrical current to motor 42 of the associated actuator 40*a* or 40*b*. Control unit 80 may accordingly include one or more motor driver or controller in communication with processor 82 and memory 84 for executing such electrical current control. Control unit 80 may then use feedback from pressure sensor 72 to adjust the speed of the rotation of the shaft of motor 42 needed to achieve a desired pressure.

FIG. 4 illustrates a draw phase, corresponding to FIG. 2, wherein positive pressure actuator 40*b* is commanded by control unit 80 to extend piston shaft 62 and piston head 64, forcing incompressible driving fluid 12, e.g., oil, from cylinder 66 into dome 30*b*, pushing reusable flexible diaphragm 68 so as to close inner chamber 112*b*, which in turn squeezes the disposable incompressible fluid, e.g., saline, into inner chamber 112*a* to inflate volumes or spheres 114, expanding or pushing apart rigid plates 116*a* and 116*b* to in turn expand flexible sheets 102*a* and 102*b*. Such action creates a negative pressure within outer chamber 110*a*, drawing (i) fresh dialysis fluid into outer chamber 110*a* (as indicated by the arrow) via supply pathways 106*a* to 106*c* or (ii) used dialysis fluid into outer chamber 110*a* (as indicated by the arrow) via patient pathway 106*d*. A corresponding pinch valve 24*a* to 24*d* is open accordingly. Pumping actuator 40*a* is commanded correspondingly by control unit

80 to retract piston shaft 62 and piston head 64 a distance, e.g., the same distance that positive pressure actuator 40*b* is moved, to allow reusable flexible diaphragm 68 to close against dome 30*a* and for incompressible driving fluid 12 to move up into cylinder 66 of actuator 40*a*.

Pressure control in the draw phase of FIG. 4 via feedback from a pressure sensor (not illustrated) provided with cylinder 66 of positive pressure actuator 40*b* is used to control the speed of motor 42 and the corresponding movement of shaft 62 and piston head 64 of positive pressure actuator 40*b*. For used dialysis fluid draw from the patient, the motor speed control is maintained so that the patient draw pressure is at or below a safe limit, e.g., −1.5 psig or less. For fresh dialysis fluid draws from a supply container (e.g., heated supply container), the pumping pressure may be higher because the patient is not involved, for example at a safe system pressure such as −5 psig or less.

FIG. 5 illustrates a discharge phase, corresponding to FIG. 3, wherein pumping actuator 40*a* is commanded by control unit 80 to extend piston shaft 62 and piston head 64, forcing incompressible driving fluid 12, e.g., oil, from cylinder 66 into dome 30*a*, pushing reusable flexible diaphragm 68 so as to close inner chamber 112*a*, which in turn squeezes the disposable incompressible fluid, e.g., saline, from inner chamber 112*a* into inner chamber 112*b* to deflate volumes or spheres 114, pushing rigid plates 116*a* and 116*b* together, to in turn push together sheets 102*a* and 102*b*. Such action creates a positive pressure within outer chamber 110*a*, pushing (i) fresh dialysis fluid from outer chamber 110*a* (as indicated by the arrow) via supply pathway 106*a* (for batch heating) or via patient pathway 106*d* (for treatment) or (ii) used dialysis fluid from outer chamber 110*a* (as indicated by the arrow) via drain pathway 106*e* to a drain. Corresponding pinch valve 24*a*, 24*d* or 24*e* is open accordingly. As described herein, where batch heating is provided, one of the supply containers, such as the supply container connected to supply container tube 108*a*, may be a dedicated batch heating container. In such a case, the dedicated batch heating container becomes a fresh dialysis fluid destination (e.g., supply pathway 106*a*).

In FIG. 5, positive pressure actuator 40*b* is commanded correspondingly by control unit 80 to retract piston shaft 62 and piston head 64 a distance, e.g., the same distance that pumping actuator 40*a* is moved, to allow reusable flexible diaphragm 68 to close against dome 30*b* and for incompressible driving fluid 12 to move up into cylinder 66 of actuator 40*b*.

Pressure control in the discharge phase of FIG. 5 via feedback from pressure sensor 72 is used to control the speed and shaft position of motor 42 and the corresponding movement of shaft 62 and piston head 64 of positive pressure actuator 40*b*. For fresh, heated dialysis fluid discharge to the patient, the motor speed control and shaft position control is maintained so that the patient fill pressure is at or below a safe limit, e.g., three psig or less. For fresh dialysis fluid discharge to a supply container for heating, the pumping pressure may be higher because the patient is not involved, for example, at a safe system pressure such as eight psig or less. For used dialysis fluid discharge to drain, e.g., a drain container or house drain, the pumping pressure may again be higher because the patient is not involved, for example, at a safe system pressure such as eight psig or less.

FIGS. 4 and 5 illustrate that system 10*a* operates with three incompressible fluids including fresh or used dialysis fluid, an incompressible driving fluid 12, such as oil, and a disposable incompressible fluid, such as saline located in first and second inner chambers 112*a* and 112*b*. In theory, when the three incompressible fluids interact, the amount of incompressible driving fluid discharged from the cylinder of the pumping linear actuator (40*b* in FIGS. 4 and 40*a* in FIG. 5) equals the amount of fresh or used dialysis fluid pulled into or discharged from outer chamber outer chamber 110*a* of the pumping set of chambers to a desired destination. The amount or volume of dialysis fluid moved is calculated by control unit 80, which knows the cross-sectional area of cylinders 66 and the distances moved via piston head 64 via feedback from encoders 44. Summing the fresh and used volumes discharged (in one embodiment only volumes pumped out of disposable set 100*a* are summed) over the course of a pumping sequence (e.g., patient fill or patient drain) via control unit 80 provides a total fresh or used dialysis fluid pumped.

It is possible however that air may be present in disposable set 100*a*, e.g., between the inner chamber 112*a* and outer chamber 110*a* or in the dialysis fluid itself. If so, and if some air is discharged from outer chamber 110*a*, then the incompressible volume calculation may be inaccurate, albeit slightly. It is accordingly contemplated for control unit 80 to run a quick test sequence both before and after the discharge stroke of pumping linear actuator 40*a* to determine if any air has been delivered. The test in both before and after instances involves closing all pinch valves 24*a* to 24*e*, such that system 10*a* is fluidically closed. Next, linear actuator 40*a* is energized to move a small amount of the incompressible driving fluid 12, e.g., 15 milliliters ("ml"), during and after which a pressure measurement is taken, e.g., via pressure sensor 72 associated with cylinder 66 of pumping linear actuator 40*a*. Before and after temperature readings from temperature sensor 74 may also be taken by control unit 80 for use in the ideal gas law calculation. If the pressure measurements taken during the movement immediately spike, then control unit 80 concludes that no or negligible air exists. Otherwise, control unit 80 uses the ideal gas law to determine the amount of air present in fluidically closed system.

If control unit 80 determines the amount of air calculated in the ideal gas law calculation in the test sequence after the discharge stroke is less than the amount of air determined in the test sequence before the discharge stroke, then it is assumed that the air difference is the amount has been delivered in the discharge stroke, wherein control unit 80 subtracts the delivered air volume from the fresh or used dialysis fluid discharge volume to determine a corrected volume of fresh or used dialysis fluid pumped.

Second Primary Embodiment

Figure 6:
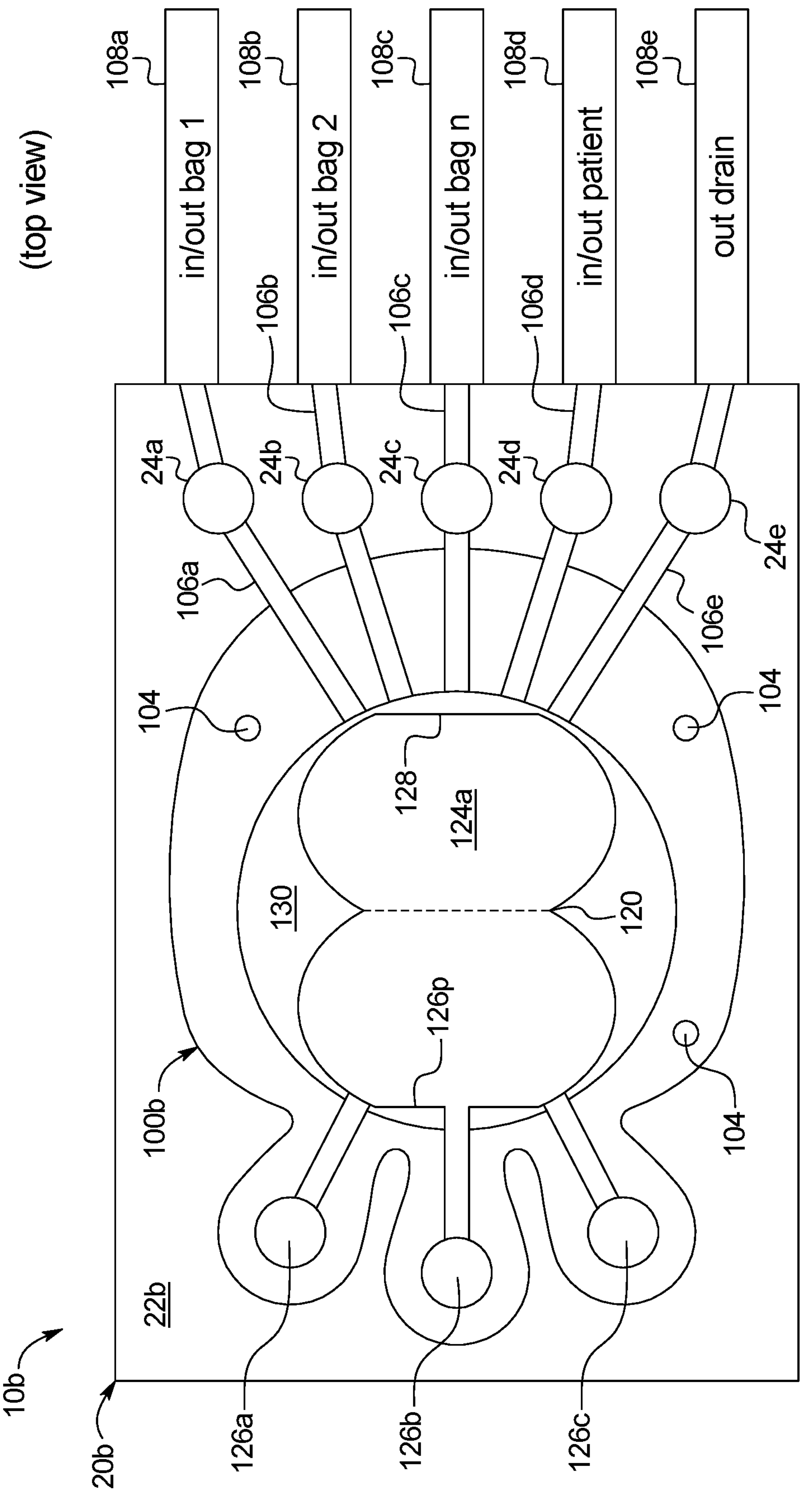
FIG. 6 is a top plan view of a second primary embodiment for an automated peritoneal dialysis ("APD") cycler and disposable set of the present disclosure.

Referring now FIGS. 6 to 12, a second automated peritoneal dialysis ("APD") system 10*b* of the present disclosure includes and APD machine or cycler 20*b* that operates with a disposable set 100*b*. In FIG. 6, APD machine or cycler 20*b* includes a housing 22*b* onto or into which disposable set 100*b* is placed for treatment. Housing 22*b* in the illustrated embodiment includes rigid structure, which may be made of a polymer or plastic, such as, polyvinyl chloride ("PVC"), polyethylene ("PE"), polyurethane ("PU") and/or polycarbonate ("PC"), and/or of metal, such as stainless steel, steel or aluminum. Disposable set 100*b* may include flexible and rigid structures that may be made of a polymer or plastic, such as any one or more of the polymers or plastics listed above.

Figure 7:
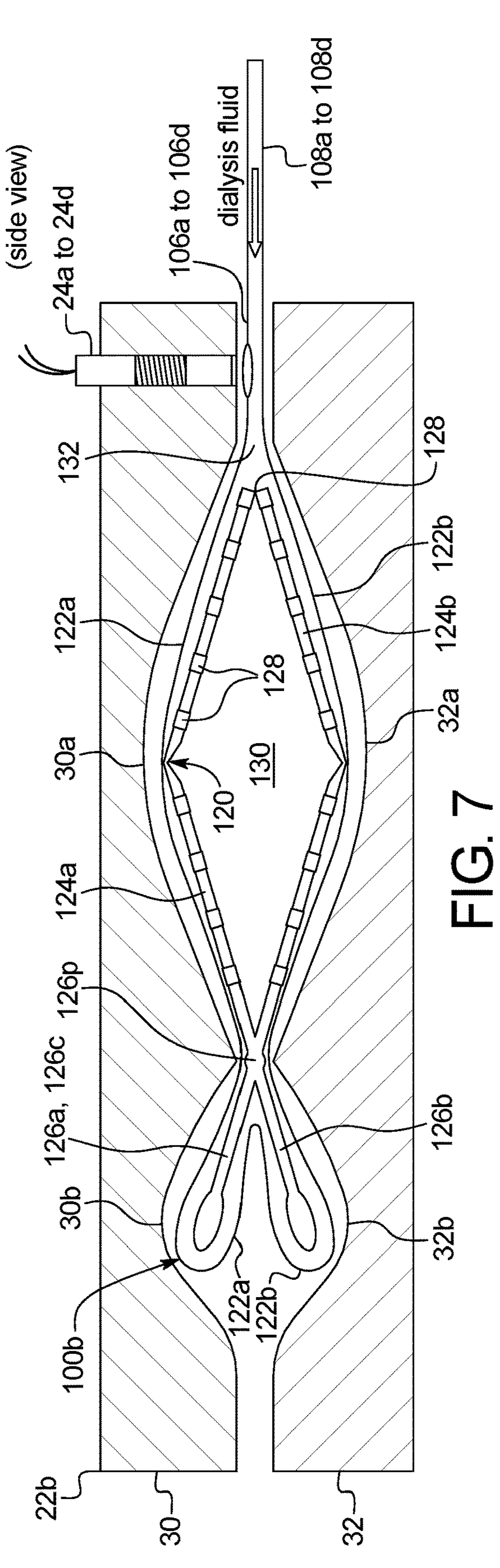
FIGS. 7 and 8 are elevation sectioned views of a relevant portion of the cycler and disposable set of the second primary embodiment of present disclosure, wherein the disposable set is in different states of operation.
Figure 8:
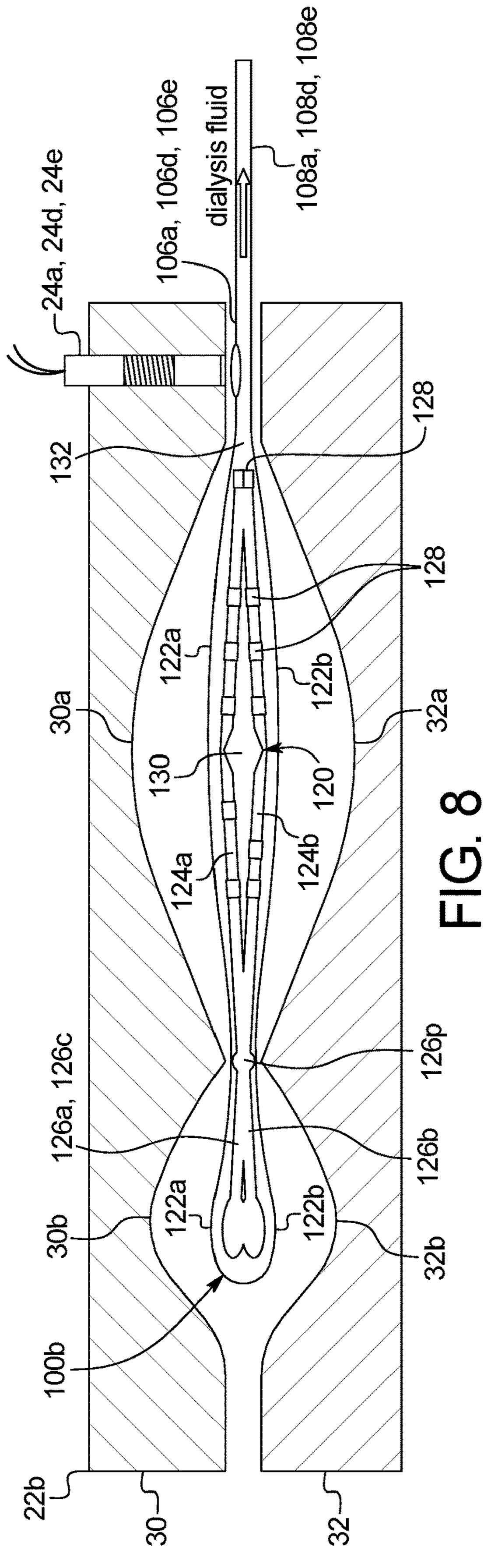

In FIGS. 6 to 8, disposable set 100*b* is at least substantially horizontally disposed on or within housing 22*a* of cycler 20*b*. Disposable set 100*a* includes outer flexible sheets 122*a* and 122*b*. Flexible sheets 122*a* and 122*b* are sealed together, e.g., ultrasonically sealed, heat sealed or solvent bonded, to form a chamber 130 for pumping fresh and used dialysis fluid (discussed below), registration holes or apertures 104 for aligning disposable set 100*a* onto housing 22*a*, and dialysis fluid pathways 106*a* to 106*e* for pumping from and to different dialysis fluid sources and destinations, respectively. In an alternative embodiment, dialysis fluid pathways 106*a* to 106*e* may instead be ports that connect to the ends of lines or tubes 108*a* to 108*e*. Tubes 108*a* to 108*e* are, as before, dialysis fluid supply container tubes 108*a* to 108*c* leading to dialysis fluid supply containers (not illustrated), a patient tube 108*d* leading to a patient connector (not illustrated), and a drain tube 108*e* leading to a drain, such as a drain container or a house drain, e.g., toilet, bathtub, etc.

Dialysis fluid lines or tubes 108*a* to 108*e* in the illustrated embodiment provide locations that operate with cycler valves 24*a* to 24*e*, respectively, which may be electrically actuated solenoid punch valves, e.g., spring closed and electrically actuated open for fail safe operation upon power loss. It should be appreciated that while dialysis fluid pathways 106*a* to 106*e* are illustrated as individually communicating fluidly with chamber 130, dialysis fluid pathways 106*a* to 106*e* alternatively communicate with a manifold line, which in turn communicates with chamber 130 via a single inlet/outlet.

FIGS. 6 to 8 illustrate disposable set 100*b* and its mounting for operation within housing 22*b* in detail. FIGS. 7 and 8 illustrate that housing 22*b*, like housing 22*a*, includes clamshell halves 30 and 32 that closed together about disposable set 100*b*. Clamshell halves 30 and 32 may hinge together and apart or translate together and apart. In the illustrated embodiment, upper clamshell half 30 includes or defines inwardly extending domes 30*a* and 30*b*, while lower clamshell half 32 includes or defines inwardly extending domes 32*a* and 32*b*. Domes 30*a* and 32*a* are aligned with corresponding chamber 130 of disposable set 100*b*. Domes 30*b* and 32*b* provide an open space for actuating a disposable linkage discussed in detail below.

In FIGS. 7 and 8, flexible sheets 122*a* and 122*b* are sealed to form chamber 130 that fits between domes 30*a* and 32*a*. As described below, chamber 130 receives fresh and used dialysis fluid. Primary differences between system 10*b* and system 10*a* are (i) disposable incompressible fluid 12 of system 10*a* is not needed or used and thus disposable set 100*b* of system 10*b* does not require inner and outer chambers and (ii) positive pressure linear actuator 40*b* of system 10*a* is replaced with an expander motor that drives a mechanical linkage (discussed below) to expand one or more rigid expander plates 124*a*, 124*b* of a disposable linkage 120 for opening chamber 130 to receive fresh or used dialysis fluid. The one or more rigid expander plates 124*a*, 124*b* of disposable linkage 120 is/are closed or compressed by the same pumping actuator 40*a* discussed above for system 10*a* to allow chamber 130 to close or be compressed to discharge or deliver fresh or used dialysis fluid.

Disposable linkage 120 may be rigid and be made of any of the materials discussed herein. FIGS. 6 to 8 illustrate that disposable linkage 120 is sealed and thus sterilized within sealed flexible sheets 122*a* and 122*b*. Disposable linkage 120 includes one or more lever arm, e.g., lever arms 126*a* to 126*c*. Lever arms 126*a* to 126*c* in the illustrated embodiment come together at a pivot 126*p*. One or more rigid expander plates 124*a*, 124*b* extend from the other side of pivot 126*p*. In this manner the mechanical expansion of lever arms 126*a* to 126*c* causes a corresponding expansion of expander plates 124*a*, 124*b* about pivot 126*p*. The compression of expander plates 124*a*, 124*b* by pumping actuator 40*a* corresponds with a like compression and resetting of lever arms 126*a* to 126*c*.

FIGS. 7 and 8 illustrate that one or more rigid expander plates 124*a*, 124*b* may include or define apertures 128 to allow fresh and used dialysis fluid into and out of chamber 130. FIG. 6 illustrates that an elongated opening 128 may alternatively or additionally be formed along the leading edge of expander plates 124*a*, 124*b* to allow fresh and used dialysis fluid into and out of chamber 130. In a similar manner, one or more opening 132 is formed in otherwise sealed flexible sheets 122*a* and 122*b* to allow fresh and used dialysis fluid into and out of chamber 130. Valves 24*a* to 24*e* control the direction in which dialysis fluid flows within opening 132.

Figure 9:
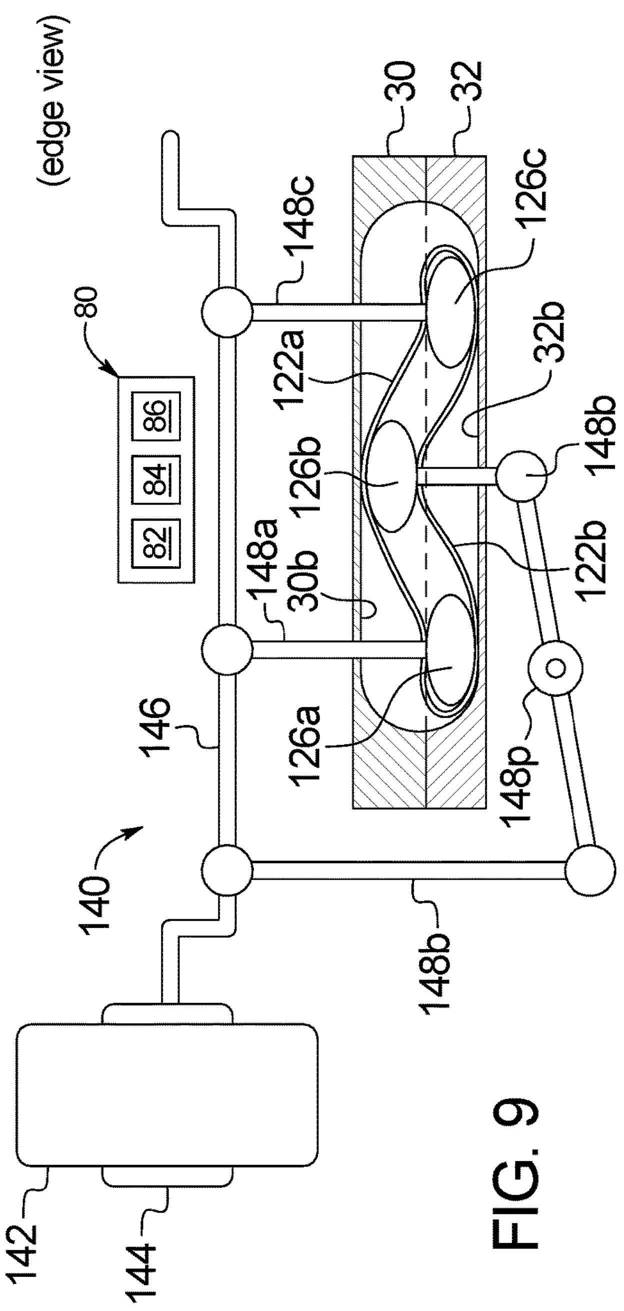
FIGS. 9 and 10 are schematic views of one embodiment for a positive pressure actuator operable with the second primary embodiment of the present disclosure.
Figure 10:
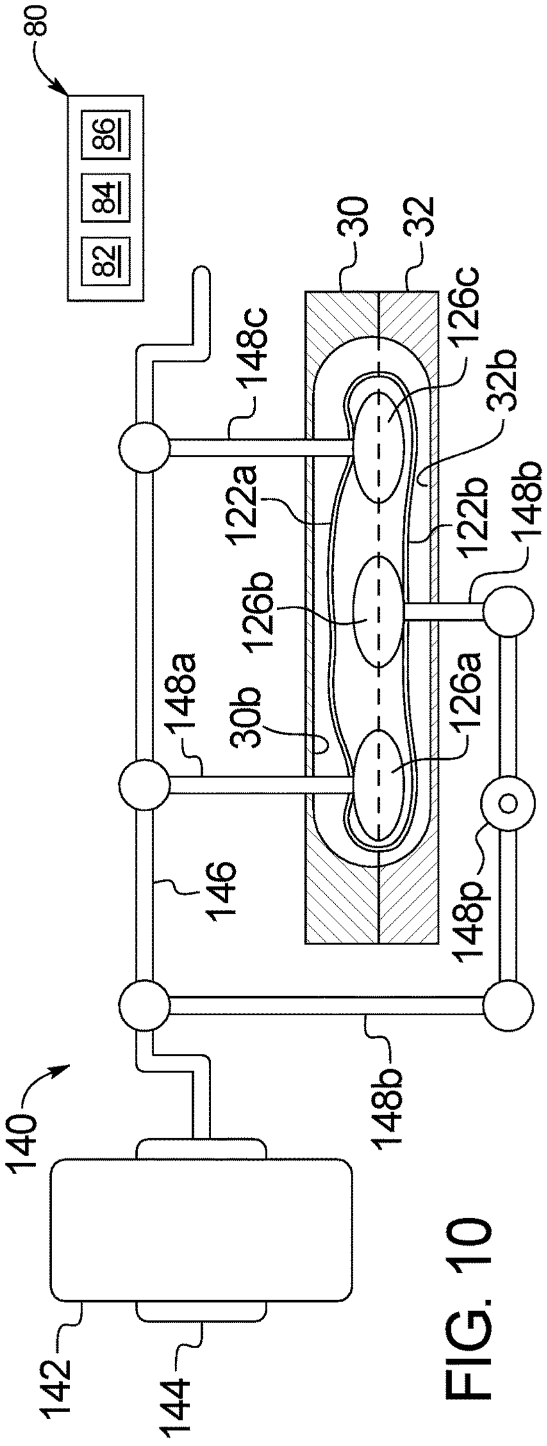

When disposable set 100*b* is mounted into APD cycler 20*b*, disposable linkage 120 is placed in mechanical communication with a motor-driven mechanical linkage 140 of cycler 20*b*. FIGS. 9 and 10 illustrate one possible embodiment for motor-driven mechanical linkage 140. Motor-driven mechanical linkage 140 in the illustrated embodiment includes motor 142, which may be a stepper, servo, brushed or brushless AC or DC motor operable with an encoder 144, which outputs to control unit 80 a signal indicative of how much a crank shaft 146 coupled to motor 142 has actually turned.

Crank shaft 146 as illustrated is connected rotatably to lever arm drivers 148*a* to 148*c*, which contact and expand lever arms 126*a* to 126*c*, respectively, in FIG. 9 when motor 142 is actuated by control unit 80 in an expansion direction by a precise amount. In FIG. 10, pumping actuator 40*a* resets lever arms 126*a* to 126*c* on the pump-out stroke. In an embodiment, since only an expansion force is applied by the lever arms to disposable linkage 120, motor 142 may be actuated by control unit 80 in a reset rotation by a precise amount, e.g., the same precise amount, before or during the actuation of pumping actuator 40*a*. That is, the reset rotation of the lever arms and the actuation of pumping actuator 40*a* do not have to be performed simultaneously. The reset may be performed earlier. Lever arm driver 148*b* in FIGS. 9 and 10 illustrates that any of lever arm drivers 148*a* to 148*c* may include or require one or more rotating pivot 148*p*, which includes a central post or pin that is fixed to a wall, frame or other structurally sound component of, or housed within, housing 22*b* of cycler 20*b*. Rotating pivot 148*p* and multiple members of lever arm driver 148*b* enable the lever arm driver to push disposable lever arm 126*b* in an opposite direction than the direction in which disposable lever arms 126*a* and 126*c* are pushed, causing the expansion of disposable linkage 120 in FIG. 9 and the corresponding expansion of chamber 130 in FIG. 7.

Lever arm drivers 148*a* to 148*c* contact disposable lever arms 126*a* and 126*c* on the opposite outsides of flexible sheets 122*a* and 122*b*, such that the sterility inside the flexible sheets is not compromised. Disposable lever arms 126*a* and 126*c* may nevertheless include or define indents or catches that hold and steady protrusions provided on the contacting ends of lever arm drivers 148*a* to 148*c*, albeit on the opposite sides of the intervening flexible sheets 122*a* and 122*b*. In an alternative embodiment, disposable lever arms 126*a* and 126*c* provide the protrusions or male members while lever arm drivers 148*a* to 148*c* provide the indents or female members.

FIG. 10 illustrates crank shaft 146 and lever arm drivers 148*a* to 148*c* having been returned to a closed or compressed position. As discussed herein, pumping actuator 40*a* resets disposable lever arms 126*a* to 126*c*, while motor 142 is actuated by control unit 80 in a reset rotation to allow the closing of chamber 130. Because disposable lever arms 126*a* to 126*c* are driven by positive pressure in FIG. 10 to close or compress chamber 130, lever arm drivers 148*a* to 148*c* are not required to grasp and pull disposable lever arms 126*a* to 126*c*, which could puncture or disrupt the integrity of intervening flexible sheets 122*a* and 122*b*.

Figure 11:
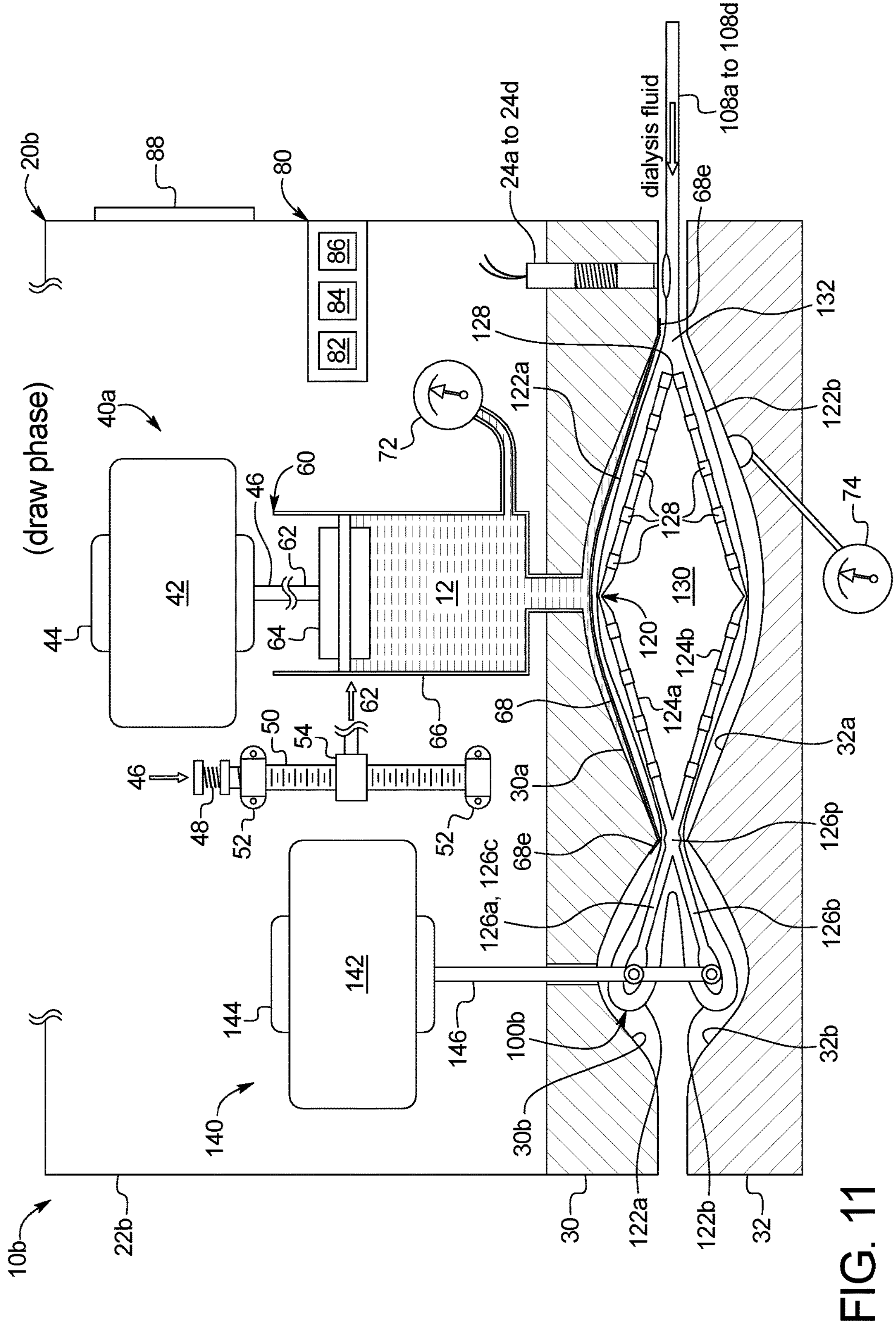
FIG. 11 is an elevation sectioned view of the cycler and disposable set of the second primary embodiment of present disclosure operating in a draw phase.

FIG. 11 illustrates the draw phase for system 10*b*, which corresponds to the draw phases of FIGS. 7 and 9. In FIG. 11, motor-driven mechanical linkage 140 is shown in a simplified form and pumping actuator 40*a* is provided to further illustrate the interaction between motor-driven mechanical linkage 140 and pumping actuator 40*a*. Pumping actuator 40*a* in an embodiment is the same as described above in connection with FIGS. 4 and 5, having all structure, functionality and alternatives, and which includes motor 42 operable with an encoder 44 that outputs a signal indicative of how much a shaft 46 of motor 42 has actually turned. Shaft 46 is connected to coupler 48, which is connected to ball or lead screw 50, which is fixed at both ends to housing 22*b* of cycler 20*b* via bearings 52. Motor 42 turns shaft 46, coupler 48 and ball or lead screw 50 a commanded number of revolutions and/or partial revolution. Member 54 threadingly connected to ball or lead screw 50 is in turn translated a precise distance. Encoder 44 outputs the actual turns of motor 42, which is converted to an actual distance traveled by member 54. Member 54 is connected to a shaft 62 of a piston/cylinder 60 of pumping actuator 40*a*. Shaft 62 terminates at or is connected to a piston head 64, which is sealed inside of a cylinder 66 having a known and constant internal diameter. Cylinder 66 is filled with an incompressible driving fluid 12, such as oil (e.g., silicone oil, or any of the fluids listed herein for the disposable incompressible fluid), located between the opposing side of piston head 64 from piston shaft 62 and a durable, reusable flexible diaphragm 68, which may for example be made of silicone or polyurethane rubber. Durable, reusable flexible diaphragm 68 is sealed at edge 68*e*, e.g., a circular edge, to upper clamshell half 30 so as to cover inwardly extending dome 30*a*, e.g., via an adhesive and/or mechanical sealing. Durable, reusable flexible diaphragm 68 prevents incompressible driving fluid 12 from escaping cycler 20*b*. Pressure sensor 72 is positioned to measure the pressure of incompressible driving fluid 12 within cylinder 66 of pumping actuator 40*a*. Temperature sensor 74 is positioned to measure the temperature of any air that may be present in the dialysis fluid located within chamber 130.

Motor-driven mechanical linkage 140 as discussed above includes motor 142 operable with an encoder 144, which outputs to control unit 80 a signal indicative of how much a crank shaft 146 coupled to motor 142 has actually turned. Crank shaft 146 in FIG. 11 manipulates lever arms 126*a* to 126*c* located within flexible sheets 122*a* and 122*b*. In FIG. 11, control unit 80 causes motor-driven mechanical linkage 140 to pull lever arms 126*a*, 126*c* apart from lever arm 126*b* about pivot 126*p*, which in turn causes rigid expander plates 124*a* and 124*b* to likewise open and extend apart about pivot 126*p*. With pinch valve 24*a* to 24*d* open, the expansion of expander plates 124*a* and 124*b* draws incompressible dialysis fluid (fresh dialysis fluid for valves 24*a* to 24*c* and effluent from patient for valve 24*d*) into chamber 130 as indicated by the arrow.

Pumping actuator 40*a* is commanded correspondingly by control unit 80 to retract piston shaft 62 and piston head 64 a distance, e.g., a distance corresponding to how far lever arms 126*a*, 126*c* are pulled apart from lever arm 126*b*, to allow reusable flexible diaphragm 68 to close against dome 30*a* and for incompressible driving fluid 12 to move up into cylinder 66 of actuator 40*a*.

Pressure control in the draw phase of FIG. 11 may be obtained by associating one or more load cell (not illustrated) outputting to control unit 80 with one or more of lever arms 126*a* to 126*c* and measuring the force exerted on the lever arm(s), wherein a negative dialysis fluid withdraw pressure is calculated using that force measurement(s), the dimensions of arms 126*a* to 126*c*, and area of expander plates expander plates 124*a*, 124*b*. Alternatively, negative dialysis fluid withdraw pressure may be derived (perhaps with more limited precision) by measuring the power applied to motor 142 (which here needs to be a permanent magnet motor 142 operating with encoder 144), which has a calibratable transfer function that can correlate motor torque vs. power. In either case, the derived negative fluid withdraw pressure is used as feedback to control the speed of motor 142 and the corresponding movement of crank shaft 146 of motor-driven mechanical linkage 140. For used dialysis fluid drawn from the patient, the speed control of motor 142 is maintained so that the patient draw pressure is at or below a safe limit, e.g., −1.5 psig or less. For fresh dialysis fluid draws from a supply container (e.g., heated supply container), the negative pumping pressure may be higher because the patient is not involved, for example at a safe system pressure such as −5 psig or less.

Figure 12:
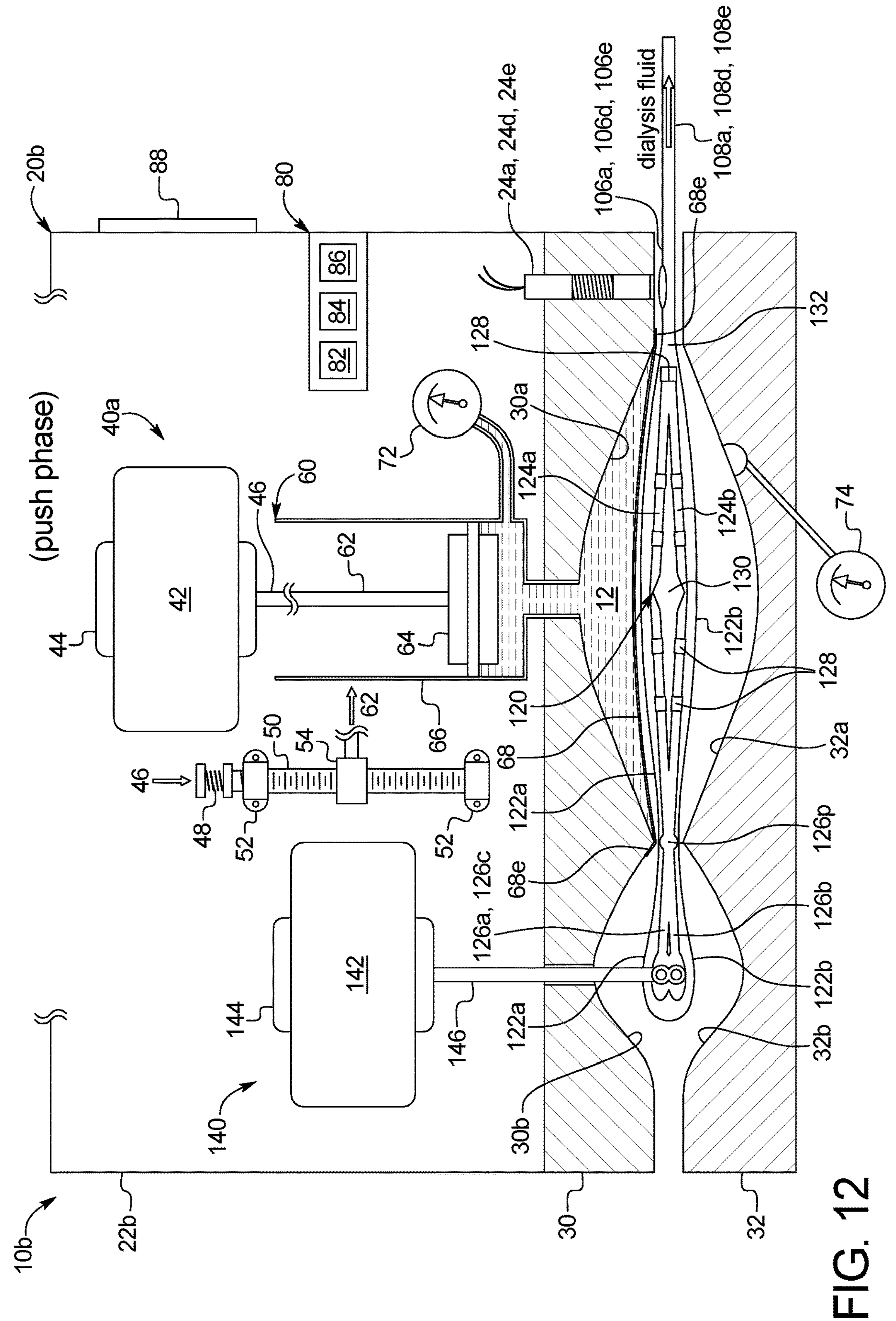
FIG. 12 is an elevation sectioned view of the cycler and disposable set of the second primary embodiment of present disclosure operating in a push or discharge phase.

FIG. 12 illustrates a discharge phase for system 10*b*, which corresponds to the discharge phases of FIGS. 8 and 10. Here, control unit 80 commands pumping actuator 40*a* to extend piston shaft 62 and piston head 64 of pumping actuator 40*a*, forcing incompressible driving fluid 12, e.g., oil, from cylinder 66 into dome 30*a*, pushing reusable flexible diaphragm 68 so as to close chamber 130, which in turn pushes (i) fresh dialysis fluid from outer chamber 110*a* (as indicated by the arrow) via supply pathway 106*a* (for batch heating) or patient pathway 106*d* or (ii) used dialysis fluid from outer chamber 110*a* (as indicated by the arrow) via drain pathway 106*e*. A corresponding pinch valve 24*a*, 24*d* or 24*e* is opened accordingly. As described herein, where batch heating is provided, one of the supply containers, such as the supply container connected to supply container tube 108*a*, may be a dedicated batch heating container. In such a case, the dedicated batch heating container becomes a fresh dialysis fluid destination (e.g., supply pathway 106*a*).

In FIG. 12, motor-driven mechanical linkage 140 is commanded correspondingly by control unit 80 to retract crank shaft 146 a distance known to correspond to the extension distance of piston shaft 62, which allows lever arms 126*a*, 126*c* and lever arm 126*b* to rotate together about pivot 126*p*.

Pressure control in the discharge phase of FIG. 12 via feedback from pressure sensor 72 is used to control the speed of motor 42 and the corresponding movement of shaft 62 and piston head 64 of pumping actuator 40*a*. For fresh, heated dialysis fluid discharge to the patient, the motor speed and shaft position control is maintained so that the patient fill pressure is at or below a safe limit, e.g., three psig or less. For fresh dialysis fluid discharge to a supply container for heating, the pumping pressure may be higher because the patient is not involved, for example, at a safe system pressure such as eight psig or less. For used dialysis fluid discharge to drain, e.g., a drain container or house drain, the pumping pressure may again be higher because the patient is not involved, for example, at a safe system pressure such as eight psig or less.

FIGS. 11 and 12 illustrate that system 10*b* operates with two incompressible fluids including fresh or used dialysis fluid and an incompressible driving fluid 12, such as oil. In theory, when the two incompressible fluids interact, the amount of incompressible driving fluid delivered to and discharged from cylinder 66 of pumping actuator 40*a* equals the amount of fresh or used dialysis fluid pulled into or discharged from chamber 130 of disposable set 100*b*. The amount or volume of dialysis fluid moved is calculated by control unit 80, which knows the cross-sectional area of cylinder 66 and the distance moved via piston head 64 via feedback from encoder 44. Summing the fresh and used volumes discharged (in one embodiment only volumes pumped out of disposable set 100*b* are summed) over the course of a pumping sequence (e.g., patient fill or patient drain) via control unit 80 provides a total fresh or used dialysis fluid pumped.

It is possible however that air may be present in disposable set 100*b*, e.g., within chamber 130 or in the dialysis fluid itself. If so, and if some air is discharged from chamber 130, then the volume calculation may be inaccurate, albeit slightly. It is accordingly contemplated for control unit 80 to run a quick test sequence both before and after the discharge stroke of pumping actuator 40*a* to determine if any air has been delivered. The test in both before and after instances involves closing all pinch valves 24*a* to 24*e*, such that system 10*b* is fluidically closed. Next, pumping actuator 40*b* is energized to move a small amount of the incompressible driving fluid 12, e.g., 15 milliliters ("ml"), during and after which a pressure measurement is taken, e.g., via pressure sensor 72 associated with cylinder 66 of pumping actuator 40*a*. Before and after temperature readings from temperature sensor 74 may also be taken by control unit 80 for use in the ideal gas law calculation. If the pressure measurements taken during the movement immediately spike, then control unit 80 concludes that no or negligible air exists. Otherwise, control unit 80 uses the ideal gas law to determine the amount of air present in fluidically closed system.

If control unit 80 determines the amount of air calculated in the ideal gas law calculation in the test sequence after the discharge stroke is less than the amount of air determined in the test sequence before the discharge stroke, then it is assumed that the air difference amount has been delivered in the discharge stroke, wherein control unit 80 subtracts the delivered air volume from the fresh or used dialysis fluid discharge volume to determine a corrected fresh or used dialysis fluid discharge volume.

It should be understood that various changes and modifications to the presently preferred embodiments described herein will be apparent to those skilled in the art. It is therefore intended that such changes and modifications be covered by the appended claims. For example, the end of a patient drain may be determined by control unit 80 detecting low effluent flowrate via the ideal gas law calculation discussed herein as opposed to draining to a prescribed drain. In another example, while the first primary embodiment is disclosed as having outer and inner chambers forming the positive pressure set of chambers, in an alternative embodiment, the outer chamber is not provided and instead only a single positive pressure chamber is provided for holding the disposable incompressible fluid, e.g., saline, and which is in incompressible fluid communication with the inner chamber of the pumping set of chambers.

The invention is claimed as follows:

1. A peritoneal dialysis system comprising:
a cycler including
a pumping actuator configured to move an incompressible fluid,
a positive pressure actuator, and
a control unit; and
a disposable set including
a chamber including an opening, and
at least one plate located within the chamber, wherein
the control unit is programmed to cause:
(i) the pumping actuator to move the incompressible fluid to discharge fresh or used dialysis fluid from the chamber through the opening, and
(ii) the positive pressure actuator to expand the at least one plate to create negative pressure within the chamber to pull fresh or used dialysis fluid into the chamber through the opening, and
wherein the pumping actuator includes a linear actuator including a piston head that moves back and forth within a cylinder, the cylinder holding the incompressible fluid between the piston head and a diaphragm.

2. The peritoneal dialysis system of claim 1, wherein the diaphragm is sealed to a dome formed in the cycler, the dome in incompressible fluid communication with the cylinder.

3. The peritoneal dialysis system of claim 1, wherein the linear actuator includes a motor that translates a member along a rotational to translational conversion device, and wherein the member is in mechanical communication with a piston shaft that moves the piston head.

4. The peritoneal dialysis system of claim 1, wherein the control unit is configured to determine a volume of the incompressible fluid moved by the pumping actuator and take the volume of the incompressible fluid moved as a volume of the fresh or used dialysis fluid discharged from the chamber.

5. The peritoneal dialysis system of claim 4, wherein the control unit is configured to determine the volume of the incompressible fluid moved by the pumping actuator by multiplying a sensed movement of the pumping actuator by a cross-sectional area of the pumping actuator.

6. The peritoneal dialysis system of claim 4, wherein the control unit is configured to reduce the volume of the fresh or used dialysis fluid discharged from the chamber by a volume of air discharged from the chamber along with the fresh or used dialysis fluid, and wherein the control unit is further configured to determine the volume of the air by taking pressure readings before and after discharging the volume of the fresh or used dialysis fluid and using the pressure readings in before and after calculations involving the ideal gas law.

7. The peritoneal dialysis system of claim 1, wherein the chamber includes a plurality of openings in fresh or used dialysis fluid communication with different sources and destinations.

8. A peritoneal dialysis system comprising:
a cycler including
a pumping actuator configured to move an incompressible fluid,
a positive pressure actuator, and
a control unit; and
a disposable set including
a chamber including an opening, and
at least one plate located within the chamber, wherein
the control unit is programmed to cause (i) the pumping actuator to move the incompressible fluid to discharge fresh or used dialysis fluid from the chamber through the opening, and (ii) the positive pressure actuator to expand the at least one plate to create negative pressure within the chamber to pull fresh or used dialysis fluid into the chamber through the opening, and wherein the positive pressure actuator includes a linear actuator including a piston head that moves back and forth within a cylinder, the cylinder holding its own incompressible fluid between the piston head and a diaphragm.

9. The peritoneal dialysis system of claim 8, wherein the diaphragm is sealed to a dome formed in the cycler, the dome in incompressible fluid communication with the cylinder.

10. The peritoneal dialysis system of claim 8, wherein the linear actuator includes a motor that translates a member along a rotational to translational conversion device, and wherein the member is in mechanical communication with a piston shaft that moves the piston head.

11. A peritoneal dialysis system comprising:

a cycler including a pumping actuator configured to move an incompressible fluid, a positive pressure actuator, and a control unit; and a disposable set including a chamber including an opening, and at least one plate located within the chamber, wherein the control unit is programmed to cause:

(i) the pumping actuator to move the incompressible fluid to discharge fresh or used dialysis fluid from the chamber through the opening, and (ii) the positive pressure actuator to expand the at least one plate to create negative pressure within the chamber to pull fresh or used dialysis fluid into the chamber through the opening, and wherein the chamber is an outer chamber, and which includes an inner chamber located within the outer chamber, and wherein the positive pressure actuator is configured to force a second incompressible fluid into the inner chamber to in turn expand the at least one plate to create negative pressure within the chamber to pull the fresh or used dialysis fluid into the chamber through the opening.

12. The peritoneal dialysis system of claim 11, wherein the inner chamber and the outer chamber form a pumping set of chambers, and wherein the disposable set includes a second inner chamber located within a second outer chamber, the second inner and outer chambers forming a positive pressure set of chambers, the second inner chamber holding the second incompressible fluid, and wherein the positive pressure actuator is configured to compress the positive pressure set of chambers to force the second incompressible fluid into the inner chamber of the pumping set of chambers.

13. The peritoneal dialysis system of claim 11, wherein the inner chamber includes a plurality of inflatable volumes in incompressible fluid communication, the inflatable volumes collectively sized to allow the fresh or used dialysis fluid to flow into the outer chamber around the outsides of the inflatable volumes.

14. The peritoneal dialysis system of claim 13, wherein the inflatable volumes include inflatable spheres.

15. The peritoneal dialysis system of claim 13, wherein the inflatable volumes collectively form a toroidal ring inside of the outer chamber.

16. A peritoneal dialysis system comprising:

a cycler including a pumping actuator configured to move a first volume of a first incompressible fluid, a positive pressure actuator configured to move a second volume of the first incompressible fluid, and a control unit; and a disposable set including an outer chamber including an opening, at least one plate located within the outer chamber, an inner chamber located within the outer chamber so as to contact the at least one plate, a positive pressure chamber in incompressible fluid communication with the inner chamber, the inner chamber and the positive pressure chamber holding a second incompressible fluid, wherein the control unit is programmed to cause:

(i) the positive pressure actuator to move the second volume of the first incompressible fluid to close the positive pressure chamber, thereby forcing the second incompressible fluid into the inner chamber to expand the at least one plate to create negative pressure within the outer chamber to pull fresh or used dialysis fluid into the outer chamber through the opening, and (ii) the pumping actuator to move the first volume of the first incompressible fluid to close the outer chamber, thereby forcing fresh or used dialysis fluid out of the outer chamber through the opening.

* * * * *